United States Patent
O'Brien et al.

(10) Patent No.: US 9,237,975 B2
(45) Date of Patent: Jan. 19, 2016

(54) ABSORBENT ARTICLE WITH SIDE BARRIERS AND DECOLORIZING AGENTS

(71) Applicant: Kimberly-Clark Worldwide, Inc., Neenah, WI (US)

(72) Inventors: Sarah O'Brien, Neenah, WI (US); SangWook Lee, Seoul (KR); SiOn Choi, GyeongGi-do (KR); Marcela Rendon, Bogata (CO); Jin Chen, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 131 days.

(21) Appl. No.: 14/038,852

(22) Filed: Sep. 27, 2013

(65) Prior Publication Data

US 2015/0094678 A1  Apr. 2, 2015

(51) Int. Cl.
*A61F 13/472* (2006.01)
*A61F 13/511* (2006.01)
*A61F 13/84* (2006.01)

(52) U.S. Cl.
CPC ............ *A61F 13/8405* (2013.01); *A61F 13/472* (2013.01); *A61F 13/51113* (2013.01)

(58) Field of Classification Search
CPC .................. A61F 13/53747; A61F 2013/4587; A61F 2013/51186; A61F 2013/5149; A61F 2013/53445; A61F 13/494; A61F 13/475; A61F 13/4751; A61F 13/4752; A61F 13/4753; A61F 13/4756; A61F 13/4758; A61F 2013/8438; A61F 2013/8441; A61F 2013/8447
USPC ........................................................ 604/367
See application file for complete search history.

(56) References Cited

U.S. PATENT DOCUMENTS 2,236,529 A    4/1941 Epstein et al.
2,418,907 A    4/1947 Schreiber
(Continued)

FOREIGN PATENT DOCUMENTS

EP    0019371 A1    11/1980
EP    0355842 A2    2/1990
(Continued)

OTHER PUBLICATIONS

International Search Report and Written Opinion for PCT/IB2014/063968 dated Dec. 26, 2014, 13 pages.
(Continued)

*Primary Examiner* — Lynne Anderson
*Assistant Examiner* — Peter S Vasat
(74) *Attorney, Agent, or Firm* — Dority & Manning, P.A.

(57) ABSTRACT

A feminine care absorbent article having fluid barrier and decolorizing structures is described. Such structures can prevent the spread of menses fluid towards the edges of the article and can also decolorize stains so that the stains are less noticeable. The article includes a liquid permeable topsheet having a central layer positioned adjacent opposing side layers. The side layers can include a separating region that at least partially separates a decolorizing agent carrier material treated with a decolorizing agent from an absorbent core. At least one of the side layers can also include at least one fluid barrier region that can prevent or slow the spread of fluids from the center of the article to the edges. The combination of the separating and fluid barrier regions can allow the decolorizing agent to sufficiently decolorize a fluid insult that may have spread to the lateral edges of the article.

17 Claims, 19 Drawing Sheets

(56) References Cited

U.S. PATENT DOCUMENTS

| | | |
|---|---|---|
| 2,542,909 A | 2/1951 | De Wet |
| 3,124,135 A | 3/1964 | Olson |
| 3,287,222 A | 11/1966 | Larde et al. |
| 3,338,992 A | 8/1967 | Kinney |
| 3,341,394 A | 9/1967 | Kinney |
| 3,347,236 A | 10/1967 | Torr |
| 3,397,697 A | 8/1968 | Rickard |
| 3,398,097 A | 8/1968 | Kersnar et al. |
| 3,490,454 A | 1/1970 | Goldfarb et al. |
| 3,502,538 A | 3/1970 | Petersen |
| 3,502,763 A | 3/1970 | Hartmann |
| 3,542,615 A | 11/1970 | Dobo et al. |
| 3,635,828 A | 1/1972 | Benjamin et al. |
| 3,663,445 A | 5/1972 | Augustin et al. |
| 3,692,618 A | 9/1972 | Dorschner et al. |
| 3,783,872 A | 1/1974 | King |
| 3,802,817 A | 4/1974 | Matsuki et al. |
| 3,814,101 A | 6/1974 | Kozak |
| 3,849,241 A | 11/1974 | Butin et al. |
| 3,953,351 A | 4/1976 | Keller |
| 3,979,318 A | 9/1976 | Tokiwa et al. |
| 4,100,324 A | 7/1978 | Anderson et al. |
| 4,190,563 A | 2/1980 | Bosley et al. |
| 4,250,257 A | 2/1981 | Lee et al. |
| 4,259,383 A | 3/1981 | Eggensperger et al. |
| 4,288,225 A | 9/1981 | Roland et al. |
| 4,340,563 A | 7/1982 | Appel et al. |
| 4,357,939 A | 11/1982 | Jackson et al. |
| 4,363,322 A | 12/1982 | Andersson |
| 4,381,784 A | 5/1983 | Aberson et al. |
| 4,431,560 A | 2/1984 | Lake et al. |
| 4,532,232 A | 7/1985 | Larsson et al. |
| 4,585,650 A | 4/1986 | Newberry, Jr. et al. |
| 4,594,327 A | 6/1986 | Zuk |
| 4,636,209 A | 1/1987 | Lassen |
| 4,655,759 A | 4/1987 | Romans-Hess et al. |
| 4,673,524 A | 6/1987 | Dean |
| 4,693,713 A | 9/1987 | Chmelir et al. |
| 4,773,423 A | 9/1988 | Hakky |
| 4,798,603 A | 1/1989 | Meyer et al. |
| 4,801,494 A | 1/1989 | Datta et al. |
| 4,803,153 A | 2/1989 | Shibata et al. |
| 4,847,089 A | 7/1989 | Kramer et al. |
| 4,855,108 A | 8/1989 | Masuda et al. |
| 4,886,512 A | 12/1989 | Damico et al. |
| 4,892,534 A | 1/1990 | Datta et al. |
| 4,908,026 A | 3/1990 | Sukiennik et al. |
| 4,933,092 A | 6/1990 | Aunet et al. |
| 5,009,716 A | 4/1991 | Gerson |
| 5,037,412 A | 8/1991 | Tanzer et al. |
| 5,064,541 A | 11/1991 | Jeng et al. |
| 5,118,428 A | 6/1992 | Sand et al. |
| 5,147,698 A | 9/1992 | Cole |
| 5,223,284 A | 6/1993 | Kulczycki et al. |
| 5,248,309 A | 9/1993 | Serbiak et al. |
| 5,262,153 A | 11/1993 | Mishima et al. |
| 5,281,208 A | 1/1994 | Thompson et al. |
| 5,284,703 A | 2/1994 | Everhart et al. |
| 5,340,493 A | 8/1994 | Principato |
| 5,340,495 A | 8/1994 | Mulcahy et al. |
| 5,350,624 A | 9/1994 | Georger et al. |
| 5,382,400 A | 1/1995 | Pike et al. |
| 5,389,282 A | 2/1995 | Saijo et al. |
| 5,401,267 A | 3/1995 | Couture-Dorschner et al. |
| 5,407,442 A | 4/1995 | Karapasha |
| 5,415,640 A | 5/1995 | Kirby et al. |
| 5,434,059 A | 7/1995 | Balaraman et al. |
| 5,447,689 A | 9/1995 | Gibboni et al. |
| 5,505,720 A | 4/1996 | Walters et al. |
| 5,527,892 A | 6/1996 | Borsotti et al. |
| 5,558,659 A | 9/1996 | Sherrod et al. |
| 5,558,834 A | 9/1996 | Chu et al. |
| 5,575,785 A | 11/1996 | Gryskiewicz et al. |
| 5,595,754 A | 1/1997 | Ito et al. |
| 5,607,414 A | 3/1997 | Richards et al. |
| 5,607,760 A | 3/1997 | Roe |
| 5,614,295 A | 3/1997 | Quincy, III et al. |
| 5,649,916 A | 7/1997 | DiPalma et al. |
| 5,652,148 A | 7/1997 | Doshi et al. |
| 5,660,798 A | 8/1997 | Doshi et al. |
| 5,695,679 A | 12/1997 | Christie et al. |
| 5,755,710 A | 5/1998 | Menard |
| 5,762,642 A | 6/1998 | Coles et al. |
| 5,766,552 A | 6/1998 | Doshi et al. |
| 5,770,543 A | 6/1998 | Garst et al. |
| 5,785,696 A | 7/1998 | Inoue et al. |
| 5,795,344 A | 8/1998 | Chappell |
| 5,807,361 A | 9/1998 | Kajikawa et al. |
| 5,810,798 A | 9/1998 | Finch et al. |
| 5,883,231 A | 3/1999 | Achter et al. |
| 5,899,893 A | 5/1999 | Dyer et al. |
| 5,912,194 A | 6/1999 | Everhart et al. |
| 5,961,505 A | 10/1999 | Coe et al. |
| 6,110,158 A | 8/2000 | Kielpikowski |
| 6,117,523 A | 9/2000 | Sugahara |
| 6,168,654 B1 | 1/2001 | Nohr et al. |
| 6,171,682 B1 | 1/2001 | Raidel et al. |
| 6,172,276 B1 | 1/2001 | Hetzler et al. |
| 6,231,719 B1 | 5/2001 | Garvey et al. |
| 6,241,714 B1 | 6/2001 | Raidel et al. |
| 6,322,544 B1 | 11/2001 | Laughlin et al. |
| 6,350,711 B1 | 2/2002 | Potts et al. |
| 6,369,293 B1 | 4/2002 | Reeves et al. |
| 6,436,080 B1 | 8/2002 | Carlucci et al. |
| 6,471,728 B2 | 10/2002 | Smith et al. |
| 6,511,465 B1 | 1/2003 | Freiburger et al. |
| 6,528,698 B2 | 3/2003 | Mizutani et al. |
| 6,534,149 B1 | 3/2003 | Daley et al. |
| 6,548,731 B2 | 4/2003 | Mizutani et al. |
| 6,559,353 B1 | 5/2003 | Sheridan |
| 6,580,015 B2 | 6/2003 | Reeves et al. |
| 6,586,653 B2 | 7/2003 | Graeme, III et al. |
| 6,613,028 B1 | 9/2003 | Daley et al. |
| 6,642,430 B1 | 11/2003 | Busam et al. |
| 6,657,098 B1 | 12/2003 | Niki et al. |
| 6,663,611 B2 | 12/2003 | Blaney et al. |
| 6,667,424 B1 | 12/2003 | Hamilton et al. |
| 6,669,932 B2 | 12/2003 | Imanaka et al. |
| 6,673,374 B2 | 1/2004 | Murad |
| 6,673,982 B1 | 1/2004 | Chen et al. |
| 6,677,498 B2 | 1/2004 | Chen et al. |
| 6,696,240 B1 | 2/2004 | Kloepfer et al. |
| 6,703,538 B2 | 3/2004 | Lassen et al. |
| 6,730,819 B1 | 5/2004 | Pesce |
| 6,812,169 B2 | 11/2004 | Potts et al. |
| 6,838,423 B2 | 1/2005 | Irvin et al. |
| 6,867,344 B2 | 3/2005 | Potts et al. |
| 6,875,617 B2 | 4/2005 | Alam |
| 6,888,044 B2 | 5/2005 | Fell et al. |
| 6,896,669 B2 | 5/2005 | Krautkramer et al. |
| 6,929,629 B2 | 8/2005 | Drevik et al. |
| 6,932,929 B2 | 8/2005 | Krautkramer et al. |
| 6,974,891 B2 | 12/2005 | Wallström |
| 6,984,770 B2 | 1/2006 | Graeme, III et al. |
| 7,105,715 B2 | 9/2006 | Carlucci et al. |
| 7,160,278 B2 | 1/2007 | Mizutani et al. |
| 7,241,627 B2 | 7/2007 | Wilhelm et al. |
| D558,335 S | 12/2007 | Willhaus |
| 7,316,673 B2 | 1/2008 | Drevik et al. |
| 7,388,123 B2 | 6/2008 | Cowell et al. |
| 7,402,157 B2 | 7/2008 | Christon et al. |
| 7,429,689 B2 | 9/2008 | Chen et al. |
| 7,431,715 B2 | 10/2008 | Guidotti et al. |
| 7,431,775 B2 | 10/2008 | Wang et al. |
| 7,504,551 B2 | 3/2009 | Herfert et al. |
| 7,687,681 B2 | 3/2010 | Di Luccio et al. |
| 7,695,726 B2 | 4/2010 | Rosevear et al. |
| 7,722,906 B2 | 5/2010 | Kandil |
| 7,723,093 B2 | 5/2010 | Kwon et al. |

(56) References Cited

U.S. PATENT DOCUMENTS

| | | |
|---|---|---|
| 7,837,944 B2 | 11/2010 | Auner et al. |
| 7,846,281 B2 | 12/2010 | Muvundamina |
| 7,879,744 B2 | 2/2011 | Seidling et al. |
| 7,928,282 B2 | 4/2011 | Dibb et al. |
| 8,003,780 B2 | 8/2011 | Kim et al. |
| 8,029,487 B2 | 10/2011 | Bagger-Sjöbäck et al. |
| 8,148,598 B2 | 4/2012 | Tsang et al. |
| 8,211,078 B2 | 7/2012 | Noel |
| 8,241,915 B2 | 8/2012 | Adamczyk et al. |
| 8,251,965 B2 | 8/2012 | Costea et al. |
| 8,283,515 B2 | 10/2012 | Lagerstedt-Eidrup et al. |
| 8,298,520 B2 | 10/2012 | Itoi et al. |
| 8,367,013 B2 | 2/2013 | Kaylor et al. |
| 8,461,411 B2 | 6/2013 | Digiacomantonio et al. |
| 8,461,412 B2 | 6/2013 | Febo et al. |
| 8,569,221 B2 | 10/2013 | Cunningham et al. |
| 8,847,002 B2 | 9/2014 | Goh et al. |
| 2002/0022813 A1 | 2/2002 | Bewick-Sonntag et al. |
| 2002/0082571 A1 | 6/2002 | Krivan et al. |
| 2002/0120242 A1 | 8/2002 | Tyrrell et al. |
| 2003/0100877 A1 | 5/2003 | Erdman |
| 2003/0114818 A1 | 6/2003 | Benecke et al. |
| 2003/0124336 A1 | 7/2003 | Keane et al. |
| 2003/0130631 A1 | 7/2003 | Springer et al. |
| 2003/0162681 A1 | 8/2003 | Hage et al. |
| 2004/0015145 A1 | 1/2004 | Miura et al. |
| 2004/0022678 A1 | 2/2004 | Komagoe et al. |
| 2004/0060112 A1 | 4/2004 | Fell et al. |
| 2005/0148488 A1 | 7/2005 | Jekel et al. |
| 2005/0256022 A1 | 11/2005 | May et al. |
| 2006/0111266 A1 | 5/2006 | Abera et al. |
| 2006/0127437 A1 | 6/2006 | Kennedy et al. |
| 2006/0189817 A1 | 8/2006 | Horlacher et al. |
| 2006/0198797 A1 | 9/2006 | Giniger |
| 2006/0222675 A1 | 10/2006 | Sabnis et al. |
| 2007/0027049 A1 | 2/2007 | Rigg |
| 2007/0055210 A1 | 3/2007 | Kao |
| 2007/0093770 A1* | 4/2007 | Ecker et al. ............. 604/385.01 |
| 2007/0116748 A1 | 5/2007 | Isele et al. |
| 2007/0122360 A1 | 5/2007 | Oniki et al. |
| 2008/0276379 A1 | 11/2008 | MacDonald et al. |
| 2008/0277621 A1 | 11/2008 | MacDonald et al. |
| 2009/0036856 A1 | 2/2009 | Woltman et al. |
| 2009/0062172 A1 | 3/2009 | Cunningham et al. |
| 2009/0062764 A1 | 3/2009 | MacDonald et al. |
| 2009/0105676 A1 | 4/2009 | Brusk et al. |
| 2009/0157021 A1 | 6/2009 | Sullivan et al. |
| 2009/0280553 A1 | 11/2009 | Mikami et al. |
| 2009/0306615 A1 | 12/2009 | Olsson |
| 2010/0028638 A1 | 2/2010 | Reichardt et al. |
| 2011/0004174 A1 | 1/2011 | Carlucci et al. |
| 2011/0251575 A1 | 10/2011 | Kuroda et al. |
| 2011/0288514 A1 | 11/2011 | Kuroda et al. |
| 2012/0109088 A1 | 5/2012 | Komatsu et al. |
| 2012/0115718 A1 | 5/2012 | Nakashita et al. |
| 2012/0141975 A1 | 6/2012 | Sato et al. |
| 2012/0165773 A1 | 6/2012 | Nakashita et al. |
| 2012/0215192 A1 | 8/2012 | Corbellini et al. |
| 2012/0296303 A1 | 11/2012 | Ng et al. |
| 2013/0012900 A1 | 1/2013 | Uda et al. |
| 2013/0158494 A1 | 6/2013 | Ong et al. |
| 2013/0261584 A1 | 10/2013 | Lee et al. |
| 2013/0261585 A1 | 10/2013 | Lee |
| 2013/0261586 A1 | 10/2013 | Lee et al. |

FOREIGN PATENT DOCUMENTS

| | | |
|---|---|---|
| EP | 0355842 A3 | 2/1990 |
| EP | 0470275 A1 | 2/1992 |
| EP | 0560630 A1 | 9/1993 |
| EP | 1034799 A1 | 9/2000 |
| EP | 1034801 A1 | 9/2000 |
| EP | 1034803 A1 | 9/2000 |
| EP | 1034804 A1 | 9/2000 |
| EP | 1358894 A1 | 11/2003 |
| EP | 1295711 B1 | 4/2006 |
| EP | 1356797 B1 | 12/2006 |
| EP | 1159014 B1 | 4/2007 |
| EP | 1842513 A1 | 10/2007 |
| EP | 2269661 B1 | 11/2012 |
| GB | 792531 A | 3/1958 |
| GB | 1349955 | 4/1974 |
| GB | 2090137 A | 7/1982 |
| GB | 2390853 A | 1/2004 |
| WF | WO2006117055 A1 | 11/2006 |
| WF | WO2011027295 A3 | 3/2011 |
| WO | WO9746219 A1 | 12/1997 |
| WO | WO9810928 A1 | 3/1998 |
| WO | WO9926588 A2 | 6/1999 |
| WO | WO9926588 A3 | 6/1999 |
| WO | WO0037039 A1 | 6/2000 |
| WO | WO0051655 A1 | 9/2000 |
| WO | WO0051656 A1 | 9/2000 |
| WO | WO0116268 A1 | 3/2001 |
| WO | WO03041752 A1 | 5/2003 |
| WO | WO03052390 A1 | 6/2003 |
| WO | WO2005107670 A2 | 11/2005 |
| WO | WO2005107670 A3 | 11/2005 |
| WO | WO2006062679 A2 | 6/2006 |
| WO | WO2006062679 A3 | 6/2006 |
| WO | WO2007085626 A1 | 8/2007 |
| WO | WO2008139340 A1 | 11/2008 |
| WO | WO2008139341 A2 | 11/2008 |
| WO | WO2008139341 A3 | 11/2008 |
| WO | WO2009027856 A2 | 3/2009 |
| WO | WO2009027856 A3 | 3/2009 |
| WO | WO 2009062998 A1 | 5/2009 |
| WO | WO 2009133518 A2 | 11/2009 |
| WO | WO 2009133518 A3 | 11/2009 |
| WO | WO2010017158 A1 | 2/2010 |
| WO | WO2011027295 A2 | 3/2011 |
| WO | WO2012074512 A1 | 6/2012 |

OTHER PUBLICATIONS

Abstract of Article—Lindon et al., "A Biological Menses Simulant Using a "Batch" Homogenization Process With Varying Levels of Rheological Properties,"IP.com, Aug. 6, 2010, 1 page.
Abstract of Chinese Patent—CN1034932, Aug. 23, 1989, 2 pages.
Abstract of Chinese Patent—CN1616115, May 18, 2005, 1 page.
Abstract of Chinese Patent—CN200948202, Sep. 19, 2007, 1 page.
Abstract of German Patent—DE102009029194, Apr. 7, 2011, 2 pages.
Abstract of Japanese Patent—JP63134050, Jun. 6, 1988, 1 page.
Abstract of Japanese Patent—JP1186809, Jul. 26, 1989, 1 page.
Abstract of Japanese Patent—JP1213231, Aug. 28, 1989, 1 page.
Abstract of Japanese Patent—JP3172400, Jul. 25, 1991, 1 page.
Abstract of Japanese Patent—JPH03215267, Sep. 20, 1991, 1 page.
Abstract of JP Patent—JP4184253, Nov. 19, 2008, 2 pages.
Abstract of Korean Patent—KR20090100645, Sep. 24, 2009, 1 page.
Abstract of WO Patent—WO 01/12241, Feb. 22, 2011, 1 page.
Machine Translation of Japanese Patent—JP07028890, 4 pages.
Article—Cacace et al., "The Hofmeister series: salt and solvent effects on interfacial phenomena," *Quarterly Reviews of Biophysics*, vol. 30, No. 3, 1997, pp. 241-277.
Article—Senczuk et al., "Hydrophobic Interaction Chromatography in Dual Salt System Increases Protein Binding Capacity," *Biotechnology and Bioenaineering*, vol. 103, No. 5, Aug. 1, 2009, pp, 930-935.
ASTM Designation: E 1164-02—*Standard Practice for Obtaining Spectrometric Data for Object-Color Evaluation*, Aug. 2002, 8 pages.
Field Guide to Stains—*How to Identify and Remove Virtually Every Stain Known to Man*, Quirk Productions, Inc., 2002, pp. 199-202.
Japanese Industrial Standard, JIS Z 8722:2000, *Methods of colour measurement—Reflecting and transmitting objects*, Revised May 20, 2000.
*On-the-spot cleanup*, Consumer Reports, Jun. 1998; p. 10.

(56) References Cited

OTHER PUBLICATIONS

*Pocket Guide to Digital Printing*, Frank Cost, Delmar Publishers, Albany, NY, ISBN 0-8273-7592-1, pp. 144-145.
*Seeing Spots? Don't Rely on Quick Stain Removers*, Consumer Reports, Aug. 2006, p. 9.
*Stain Removers: Which Are Best?*, Consumer Reports, Mar. 2000, p. 52.
Online encyclopedia article: "Oxidizer." Access Oct. 6, 2008, http://en.wikipedia.org/wiki/Oxidizer, 3 pages.
Online encyclopedia article: "Fatty acid." Accessed Oct. 6, 2008, http://en.wikipedia.org/wiki/Fatty_acid, 9 pages.

* cited by examiner

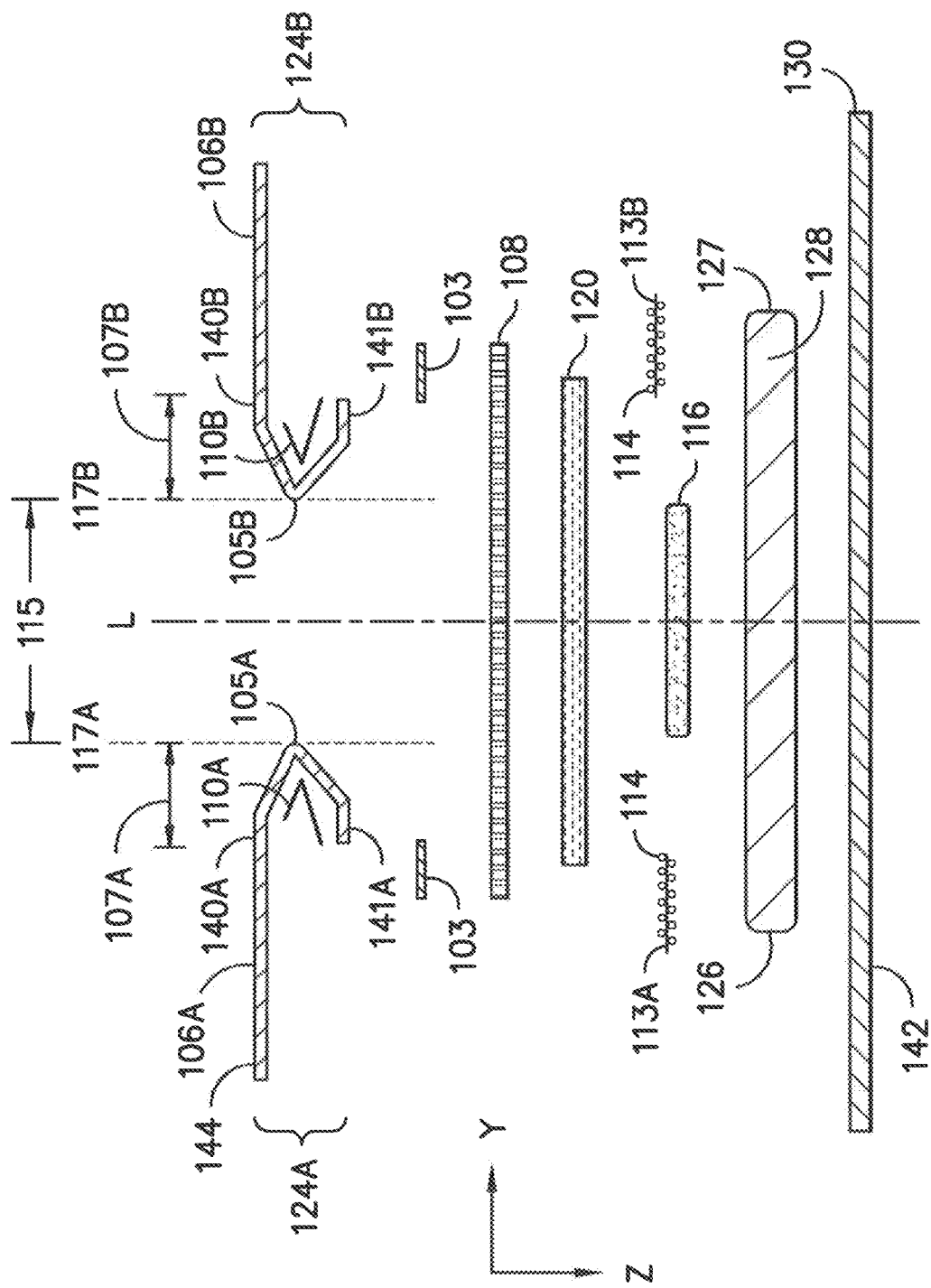
FIG. -13-

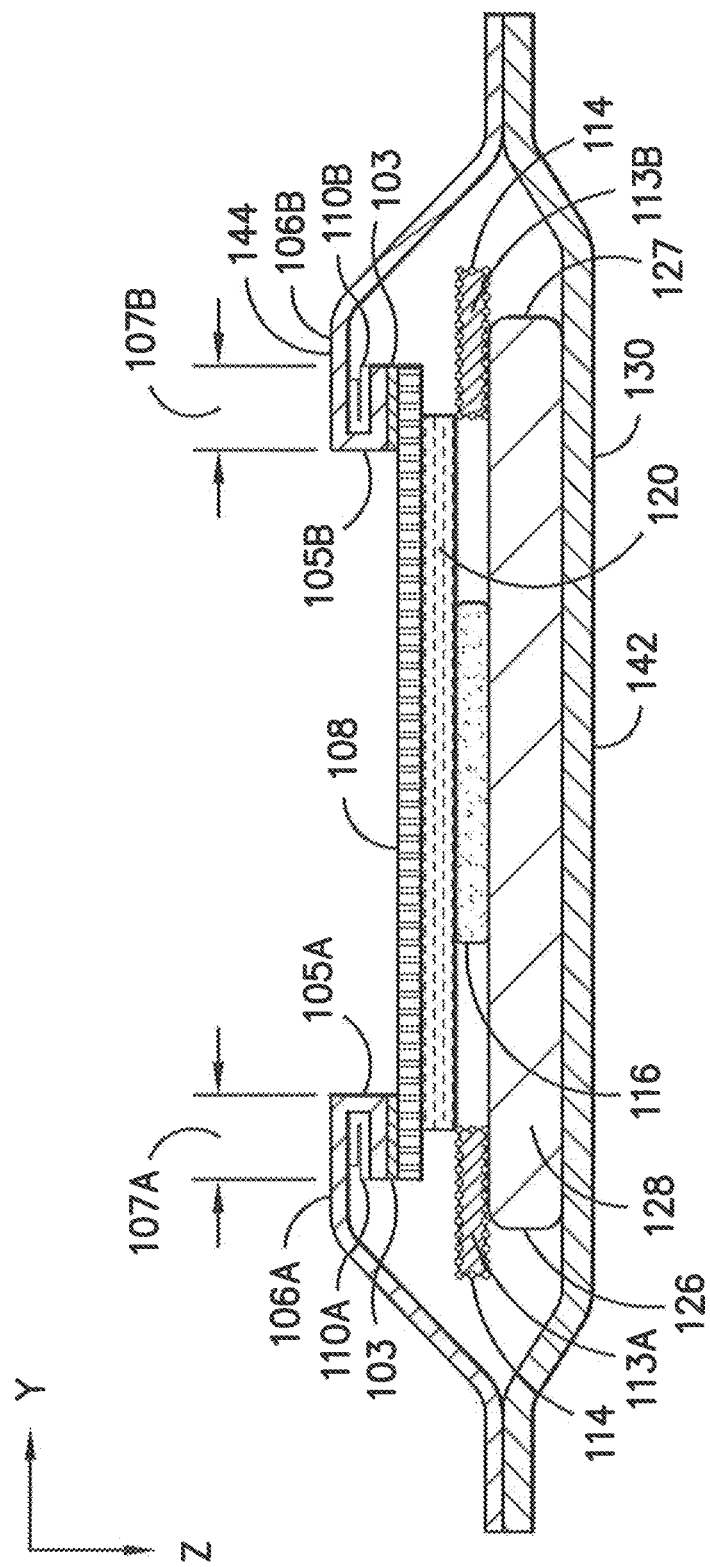
FIG. -14-

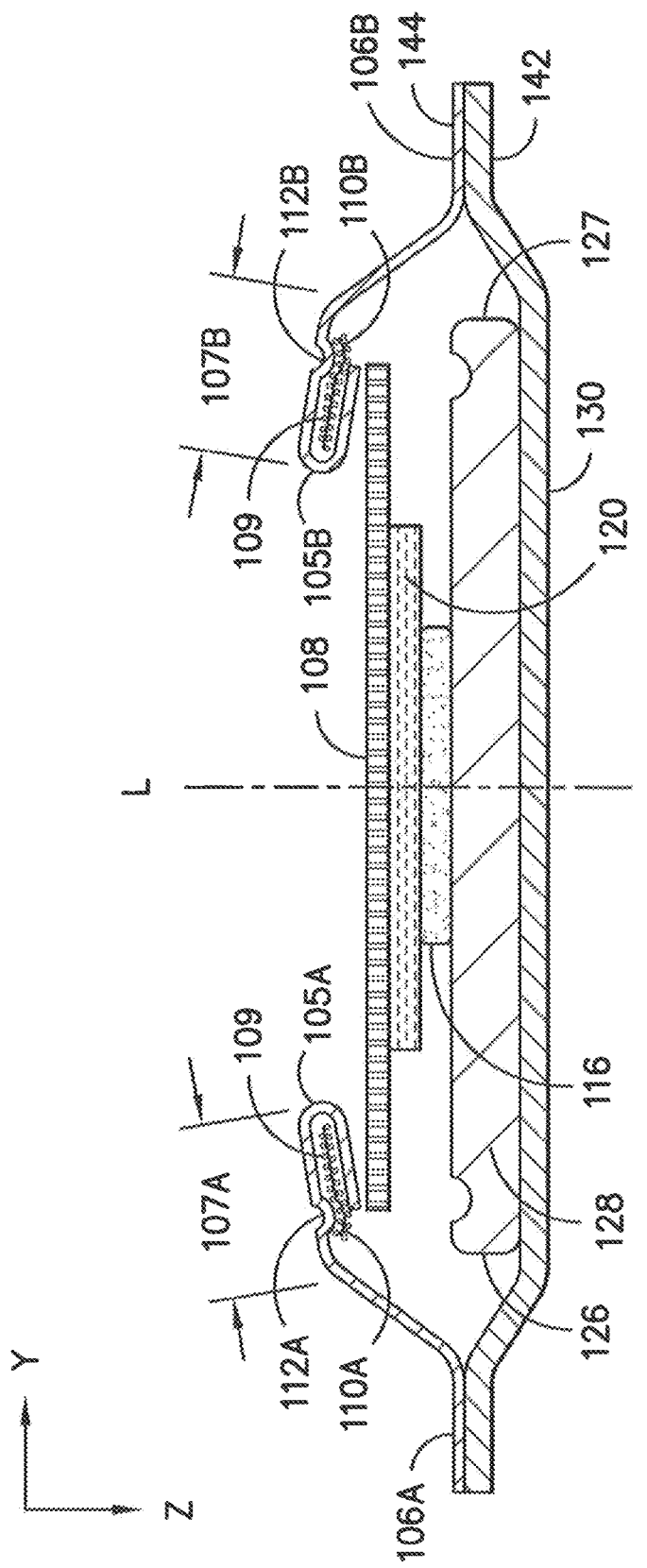
FIG. -15-

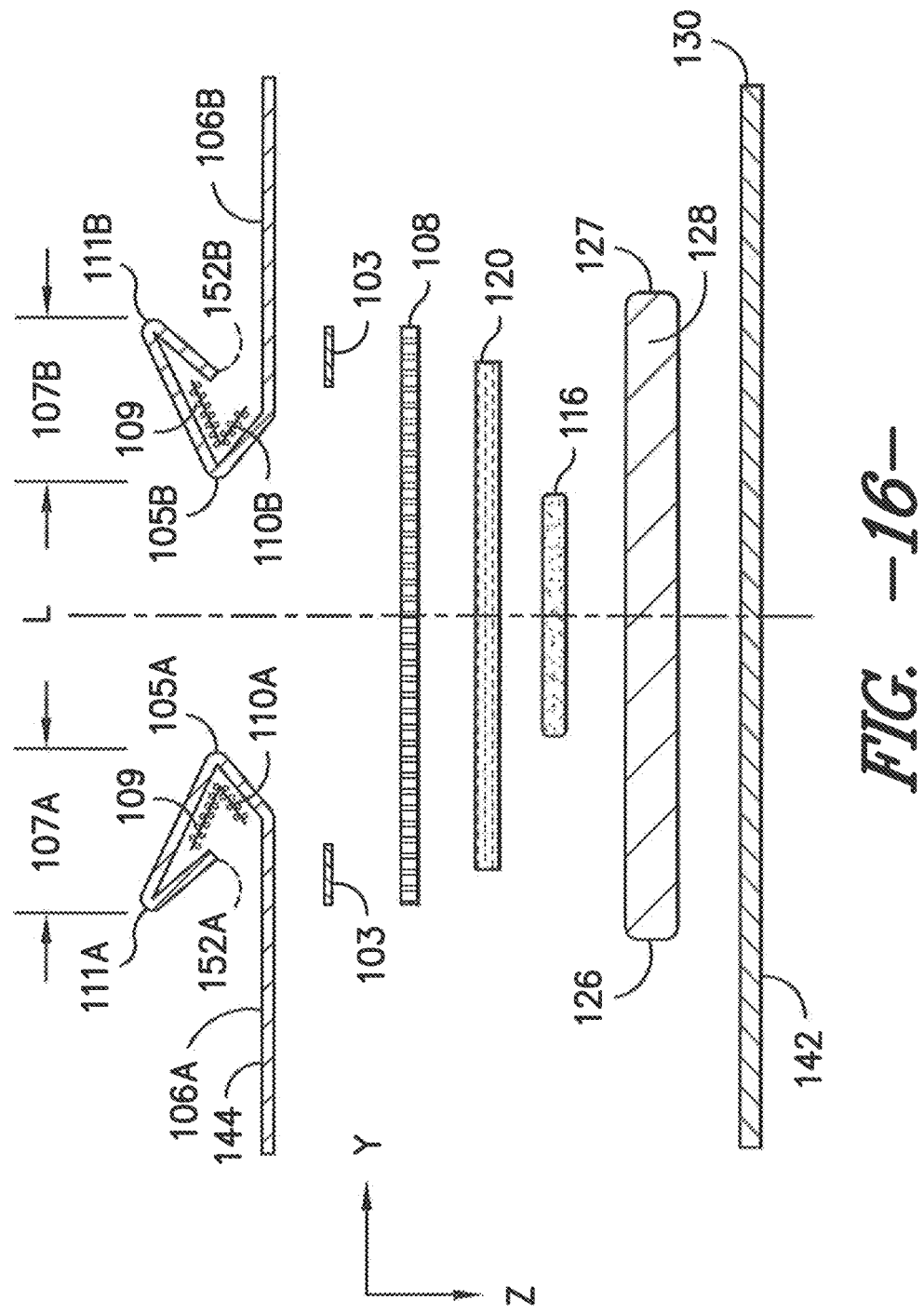
FIG. -16-

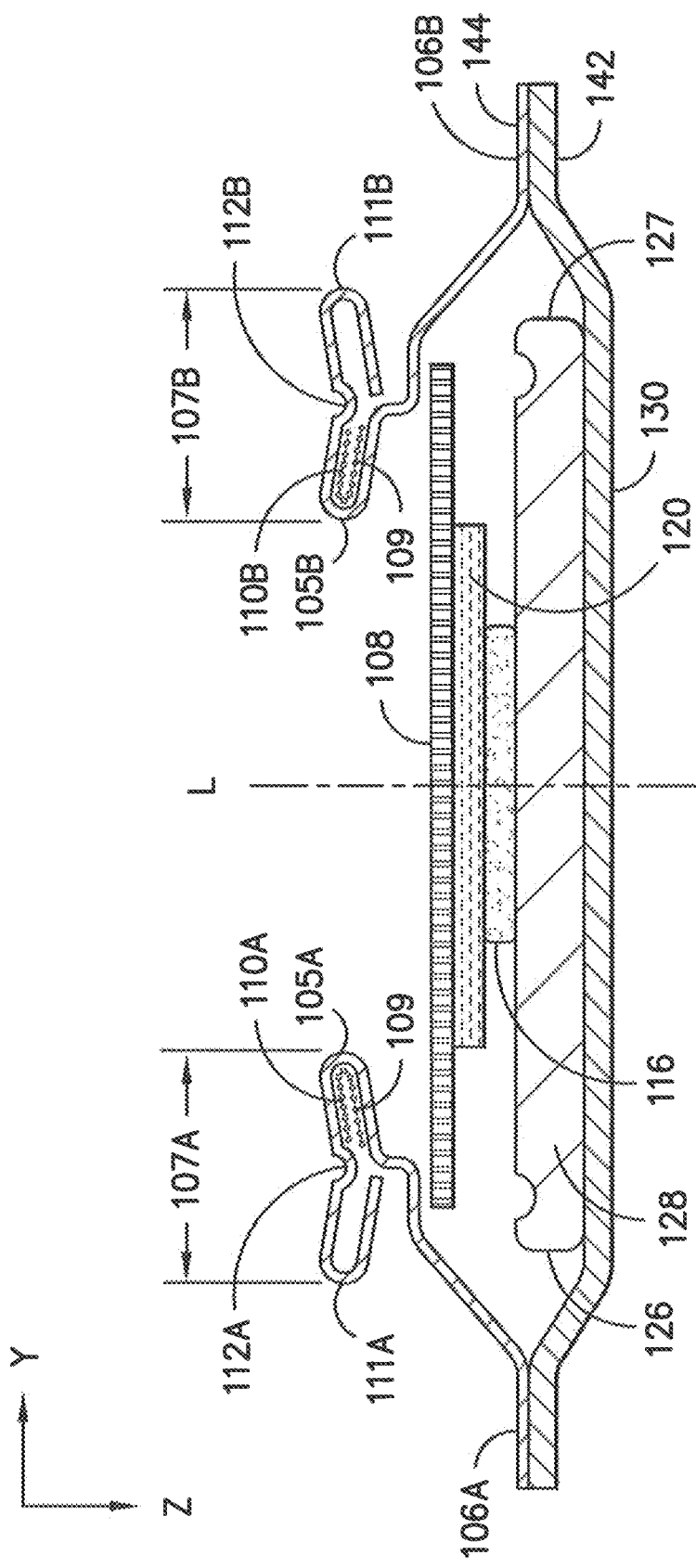
FIG. -17-

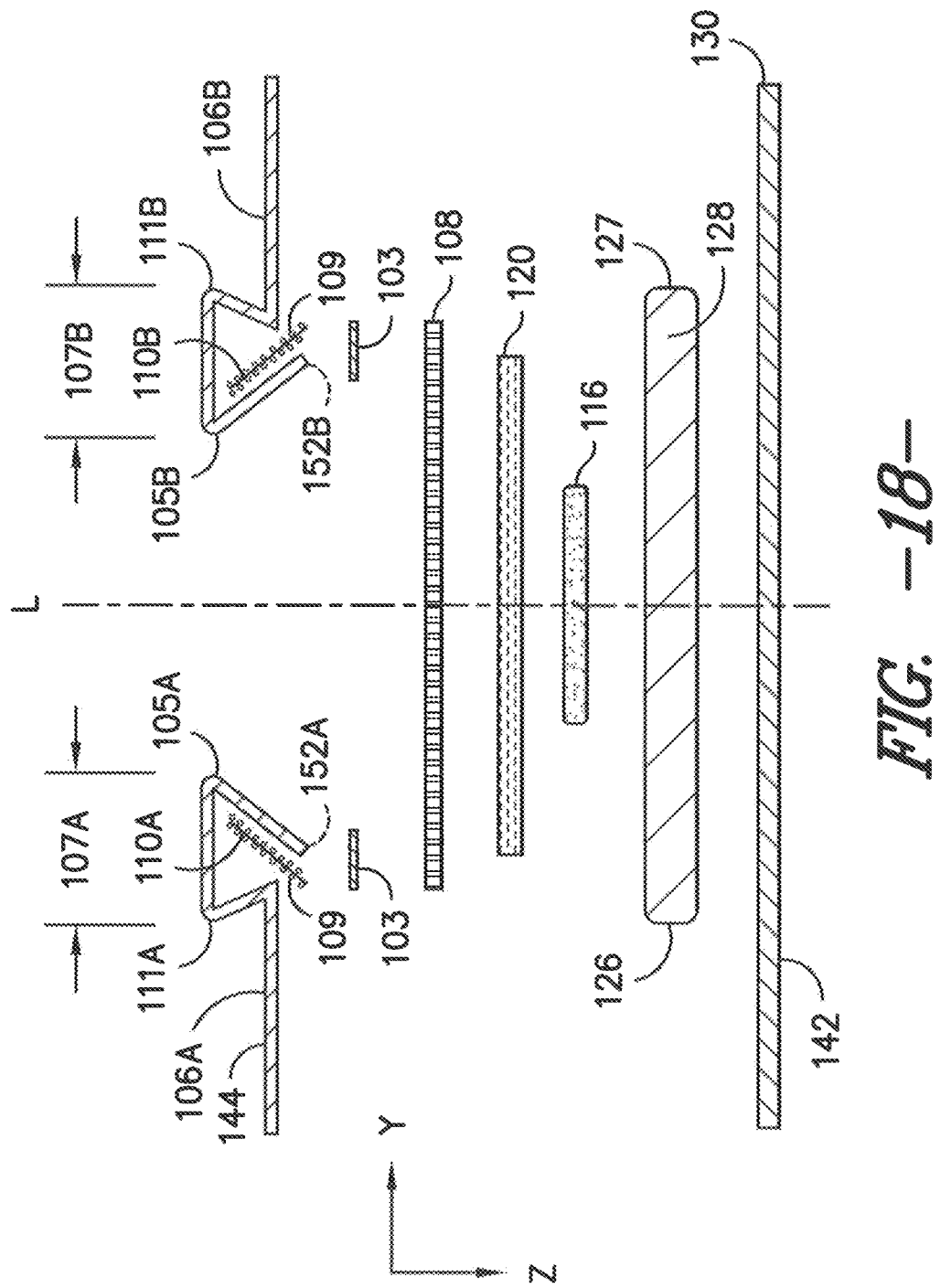
FIG. -18-

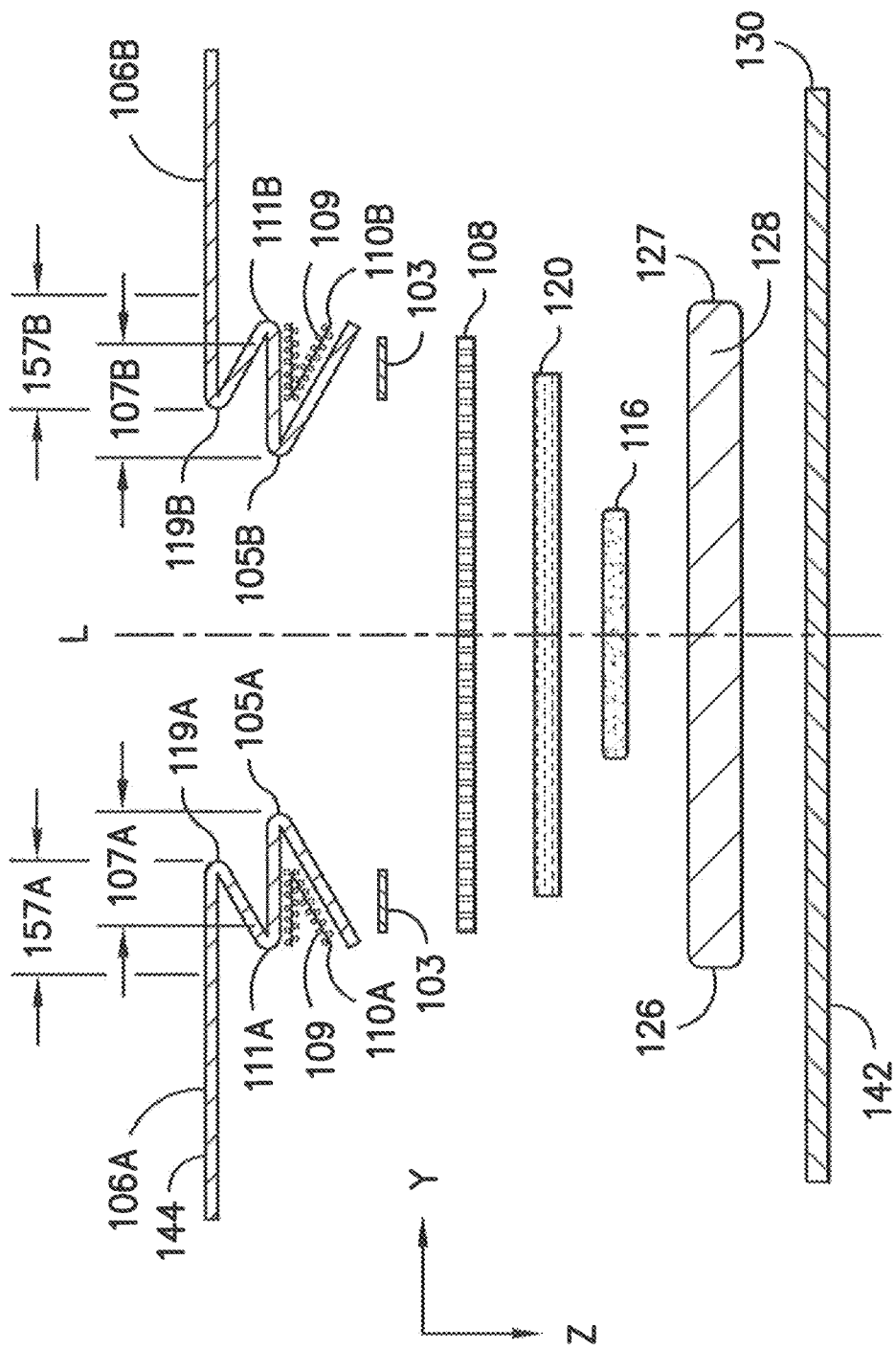
FIG. -19-

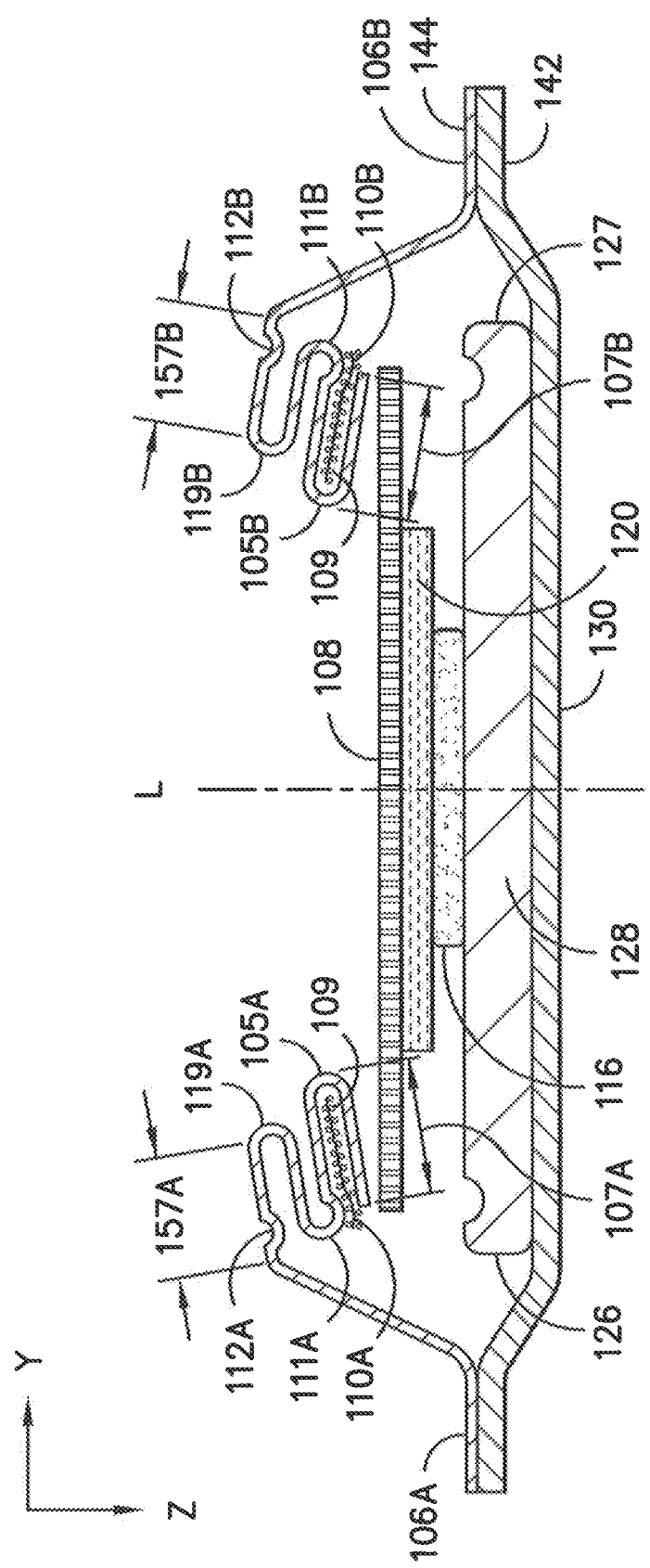
FIG. -20-

ABSORBENT ARTICLE WITH SIDE BARRIERS AND DECOLORIZING AGENTS

BACKGROUND OF THE INVENTION

Feminine care absorbent articles are often used to collect and retain body fluids, liquids, or exudates containing menses or blood. In the context of such products, comfort, absorbency, and discretion are three main product attributes and areas of concern for the wearer. In particular, wearers are often interested in knowing that such products will absorb significant volumes of menses exudates in order to protect their undergarments, outergarments, or bedsheets from staining, and that such products will help them avoid the subsequent embarrassment brought on by such staining. Wearers are also interested in using products that cannot be seen or felt through their undergarments.

Feminine care absorbent articles, such as sanitary napkins, pads and pantiliners, typically include at least one or more absorbent layers enclosed between a body-facing, liquid permeable topsheet layer and a garment-facing liquid impermeable backsheet layer. The edges of the topsheet and backsheet layers are often bonded together at their periphery to form a seal around the article to thereby contain the absorbent layers and any exudates received into the article through the topsheet. In use, such articles are typically positioned in the crotch portion of an undergarment for absorption of bodily exudates, and are held in place via adhesive strips positioned on the undersurface of the articles (facing the garment). Some of these articles also include wing-like structures for wrapping about the user's undergarments to further secure them to a user's underwear. Such wing-like structures (also known as flaps or tabs) are frequently made from lateral extensions of the topsheet and backsheet layers.

For many women, it is entirely routine to periodically view their feminine care absorbent articles during use, so as to monitor the appearance and spread of a menses insult (so as to avoid leakage throughout the day). For some women, a concern or cause of emotional discomfort with conventional feminine care absorbent articles is the expanding appearance of a menses insult in the article, and specifically, the spread of the menses stain to the side edges of a product. While many women often do not mind seeing a targeted stain in the center of a pad, and then change the pad accordingly, some women prefer not to see an extensive stain, other than the centralized insult stain. Obviously, the leakage of fluids when using such articles, particularly from around the side edges of the articles, is universally a cause of emotional concern. Such leakage may occur in the narrower product dimension along the longitudinally directed side edges, or along the wing or flap areas. Product leakage may lead not only to embarrassment for the user, but also to a general loss of confidence in use of the articles.

Various attempts have therefore been made to incorporate chemistry or structures into feminine care pads to separate staining, direct staining, target staining, mask staining or discolor menses staining; to make more efficient use of as much of an absorbent product as possible; and to reduce or prevent leakage. Such structures include embossed walls or channels, printed target areas, polymeric or other liquid impermeable barrier walls, and the like. However, such attempts have not been completely successful at eliminating or addressing the leakage problem, or reducing user concerns over staining, should it occur.

Attempts have also been made to chemically alter and separate components of menses along the depth direction of a pad, and thus reduce the mental impact of a possible stain, should menses strike through an absorbent layer to the bottom of a pad. For example, U.S. Pat. No. 3,124,135 to Olson, discloses the use of salts on a pad's interior layers (salt layer sandwiched between absorbent core layers and having the same lateral dimensions of the absorbent layers), so as to decolorize menses by precipitating the darker colored hemoglobin of the menses, as fluid travels in the depth direction of the pad. Such decolorizing allows almost clear menses liquid to flow to various portions of lower absorbent layers and away from the precipitated hemoglobin. Such decolorizing also allows clear menses liquid to potentially flow through a lower absorbent layer to the bottom of a pad, thereby reducing the occurrence of a visible stain at the bottom of a pad. The Olson reference highlights the stiffness produced in a pad as a result of the interior salt-containing layers, and offers a pad softening-solution, by use of polyethylene glycol (hereinafter PEG) as an additional element with the impregnated salt elements on the interior layers of a pad. However, even with such salt and PEG combinations, the placement of this agglomeration chemistry on, or immediately near the absorbent layers, and having the same lateral dimensions as the absorbent layers (along the depth (z) axis), can lead to the blocking of absorbency pathways in an article. Possible leakage may then result from the redirected fluid. Further, the Olson reference does not address staining that results from pad leakage off of the pad top surface, either as a result of fluid flow or saturation of a subjacent absorbent layer. Nor does the Olson reference address the concern of consumers that would rather limit their viewing of a stain in a pad, when viewing a pad from the topsheet layer surface. U.S. Patent Publication No. 2012/0165773 to Nakashita, et al. also describes placement of chemistry within the core layer. A further reference which describes an alternative technique for filtering using a "depth filter" is U.S. Pat. No. 6,350,711 to Potts, et al. Still another reference which describes the use of specific salts to remove colored substances from aqueous fluids is U.S. Patent Publication No. 2012/0215192 to Corbellini, et al. However, there is still a need to lessen leakage, and to alter the stain-producing fluid off of a feminine hygienic pad top surface, so as to lessen the mental impact of a menses insult (and potential leakage stain) for pad users, without interfering with the functioning of a product's absorbent layers; there is also a need for such alteration of the stain-producing fluid without impacting product "feel" that may be impacted by the addition of salts; and there is also a need for a pad which limits staining potential as well a consumer's view of a stain within the pad.

Numerous absorbent structures have also been developed for capturing and retaining voluminous menses exudates released by women during their monthly cycles. In this regard, the designs of such absorbent pads and pantiliners have been refined over time, so as to make their usage more comfortable (physically and emotionally) to consumers. As absorbent technology has advanced, superabsorbent polymer chemistry and substrate layering designs have been developed, enabling manufacturers to produce feminine absorbent products with progressively thinner configurations. As a result, feminine hygiene sanitary napkins, pads, and liners have become significantly thinner and more absorbent, so as to impart both comfort and a certain inconspicuousness to a wearer. For the most part, such thinner products have provided the users and surrounding third parties with the impression that the user is not wearing any form of menses protection in her undergarments.

Generally, feminine hygiene sanitary napkins, pads, and liners predominantly distribute menses laterally and longitudinally, and, when they leak, predominantly leak off the side edges (longitudinally directed sides, front, and back) rather than through the pad bottom. This leakage distribution is driven in part by not-so-close pad body fit, due to attachment to underwear or panties, and the pad construction. These pads are typically less than ¼ inch thick, have an impervious layer to impede menses and air movement through the pad, and utilize specific distribution materials to drive lateral and longitudinal distribution. Modern pads also contain superabsorbent that can interfere with the distribution of menses within the pad. The use of superabsorbent materials in core layers can lead to gel blocking that interferes with maximized fluid absorption.

Even with these advancements in absorbency, however, consumers continue to experience some leakage, typically from fluid run-off from the topsheet surface. Such run-off is often the result of various "structural" and "action-based" root causes, which cause soiling of user garments or bedding. For example, structural causes may include impeded absorbency pathways or inability to handle fluid surges. Further, consumer movements during their daily activities may cause menses exudates to leak off of the absorbent article. Therefore, despite the development of many different absorbent technologies and structural designs, product leakage and the resulting stains caused from such leakage continue to concern potential users of such products. Further, mere adaptation of older decolorizing technology to modern pad structures is not adequate to prevent locally overwhelming the decolorizing technology, as it does not account for interference from modern superabsorbents (superabsorbent competes with the decolorizing technology for the menses), lack of adequate surface area, and modern day pad menses distribution. A need therefore exists for pad constructions that prevent lateral and longitudinal distribution of the red stain of menses.

Certain sensors or condition change indicators are known for use with feminine care absorbent articles and other types of absorbent articles, to notify a user or caregiver of the impending need to change such article as a result of a change in condition. Such devices may assist in providing consumers with calmed emotional states, knowing that the devices are actively communicating impending product failure or body states. Such indicators can be seen for example in U.S. Patent Publication Nos. 2003/0130631 to Springer and 2007/0055210 to Kao. While such devices are focused primarily on preventing leakage or staining, or the onset of some other condition by limiting user wear time, such devices do not assist in altering potential staining, should leakage actually occur. There is therefore a further need for such products which would reduce consumer emotional concerns of such staining, and the embarrassment that might accompany such staining if it were to occur.

As previously described, certain chemistry for the decolorizing of blood stains on absorbent articles is known. For example, colorant changers, neutralizers or decolorizing compositions are described in U.S. Patent Publication Nos. 2008/0277621 to MacDonald, 2009/0061718 to Seidling, and 2009/0062764 to MacDonald, WO2009133518 to Cunningham, U.S. Pat. No. 6,730,819 to Pesce, U.S. Pat. No. 7,105,715 to Carlucci, and U.S. Pat. No. 3,124,135 to Olson, U.S. Patent Publication No. 2011/0004174 to Carlucci, and WO2011027295 to Corbellini, each of which are hereby incorporated by reference in their entirety. However, such chemistries are often difficult to place uniformly on a product surface, or to manipulate into a high enough surface area. Further, such chemistries may often result in a heavier, stiffer, and a subsequently more uncomfortable feeling article. Finally, such chemistries may result in menses color alterations that are less desirable to a consumer. Therefore, even with these available chemistries for decolorizing, there is a further need for absorbent structures which utilize barrier structures and decolorizing chemistry to reduce the severity/appearance of menses staining of both a user's pad, and a user's garments or bedding. There is also a need for absorbent articles which reduce a consumer's concern over any stain that might occur, as well as articles which more efficiently use absorbent systems to take up retained liquids.

SUMMARY OF THE INVENTION

In accordance with one embodiment of the present invention, a feminine care absorbent article is described that extends in a longitudinal direction, a transverse direction, and a depth direction, wherein the longitudinal direction defines a distal end and a proximal end. The feminine care absorbent article comprises a liquid permeable topsheet and a liquid impermeable backsheet. At least one layer of the topsheet defines a body-facing surface of the absorbent article, while the liquid impermeable backsheet defines a garment-facing surface of the absorbent article. The liquid permeable topsheet comprises a longitudinally extending central layer positioned adjacent a first longitudinally extending side layer and a second longitudinally extending side layer in the transverse direction, wherein the first side layer includes a first encapsulated region, and wherein the encapsulated region at least partially envelops a first decolorizing agent carrier material treated with a first decolorizing agent for decolorizing menses.

In one particular embodiment, the feminine care absorbent article can further comprise an absorbent core having first and second peripheral edges disposed between the topsheet and the backsheet in the transverse direction. In yet another embodiment, the first encapsulated region can be disposed between the first and second peripheral edges of the absorbent core in the transverse direction when viewed from the body-facing surface.

In still another embodiment, the first side layer can include at least one embossed region extending in the longitudinal direction and extending in the depth direction through at least a part of the first encapsulated region. Further, the embossed region can be present continuously from the distal end to the proximal end of the feminine care absorbent article in the longitudinal direction.

In one more embodiment, the first decolorizing agent carrier material treated with the first decolorizing agent can be free of embossing. For instance, the embossed region can be present on the first side layer at a portion that does not contain the first decolorizing agent carrier material treated with the first decolorizing agent.

In another embodiment, the first encapsulated region can be defined by a first fold located about a first fold axis, the first fold axis extending in the longitudinal direction. Further, the first decolorizing agent carrier material treated with the first decolorizing agent can have a width dimension along the transverse direction that is less than or equal to half of that of a width dimension along the transverse direction of the first encapsulated region. Moreover, the first encapsulated region can be further defined by a second fold located about a second fold axis, the second fold axis extending in the longitudinal direction. Further, the at least one embossed region can be present in only one of the first fold and the second fold.

In yet another embodiment, the first encapsulated region can envelop substantially all of the first decolorizing agent carrier material treated with the first decolorizing agent.

In still other embodiments, the first decolorizing agent can comprise polyethylene glycol, polyethylene oxide, methoxypolyethylene glycol, ammonium sulfate, zinc oxide, carbomer, or a combination thereof.

Further, in one embodiment, the first decolorizing agent carrier material can comprise a meltblown microfiber, while in another embodiment, the first decolorizing agent carrier material can comprise a through-air bonded carded web.

In one more embodiment, the second side layer can include a second encapsulated region, wherein the second encapsulated region at least partially envelops a second decolorizing agent carrier material treated with a second decolorizing agent for decolorizing menses. Additionally, the second side layer can include at least one embossed region extending in the longitudinal direction and extending in the depth direction through at least a part of the second encapsulated region.

In another embodiment, the feminine care absorbent article can further comprise an additional decolorizing agent carrier material treated with an additional decolorizing agent, wherein the additional decolorizing agent carrier material is positioned between the topsheet and backsheet in the depth direction. Meanwhile, in another embodiment, the first and second side layers can include a hydrophobic coating.

In accordance with one more embodiment of the present invention, a feminine care absorbent article is described that extends in a longitudinal direction, a transverse direction, and a depth direction, wherein the longitudinal direction defines a distal end and a proximal end. In such an embodiment, the feminine care absorbent article includes a liquid permeable topsheet defining a body-facing surface of the absorbent article, an absorbent core, and a liquid impermeable backsheet defining a garment-facing surface of the absorbent article. The liquid permeable topsheet includes a longitudinally extending central layer positioned adjacent a first longitudinally extending side layer and a second longitudinally extending side layer in the transverse direction; a separation region, wherein the separation region at least partially separates a decolorizing agent carrier material treated with a decolorizing agent from the absorbent core; and a fluid barrier region, wherein the fluid barrier region prevents the spread of fluid from a central area of the topsheet towards a lateral area of the topsheet.

In a further embodiment, the separation region can comprise a layer disposed between the decolorizing region and the absorbent core, an adhesive, a partial coating on the decolorizing region, a gap between the decolorizing region and the absorbent core, partial removal of the absorbent core, complete removal of the absorbent core, or a combination thereof.

Meanwhile, in an additional embodiment, the fluid barrier region can comprise an embossed region, a density gradient, a pore size gradient, a tortuosity gradient, a topographical gradient, a hydrophobic coating, a wettability agent, or a combination thereof.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, including reference to the appended figures, in which:

FIG. 13 is an exploded cross-sectional view of another embodiment of the absorbent article of the present disclosure taken at transverse line B of FIG. 1;

FIG. 14 is a cross-sectional view of the embodiment of the absorbent article shown in FIG. 13 after the absorbent article has been assembled;

FIG. 15 is a cross-sectional view of one embodiment of the absorbent article of the present disclosure after the absorbent article has been assembled;

FIG. 16 is an exploded cross-sectional view of one embodiment of the absorbent article of the present disclosure taken at transverse line B of FIG. 1;

FIG. 17 is a cross-sectional view of the embodiment of the absorbent article shown in FIG. 16 after the absorbent article has been assembled;

FIG. 18 is an exploded cross-sectional view of another embodiment of the absorbent article of the present disclosure taken at transverse line B of FIG. 1;

FIG. 19 is an exploded cross-sectional view of yet another embodiment of the absorbent article of the present disclosure taken at transverse line B of FIG. 1; and FIG. 20 a cross-sectional view of the embodiment of the absorbent article shown in FIG. 19 after the absorbent article has been assembled.

DETAILED DESCRIPTION OF REPRESENTATIVE EMBODIMENTS

Definitions

Figure 1:
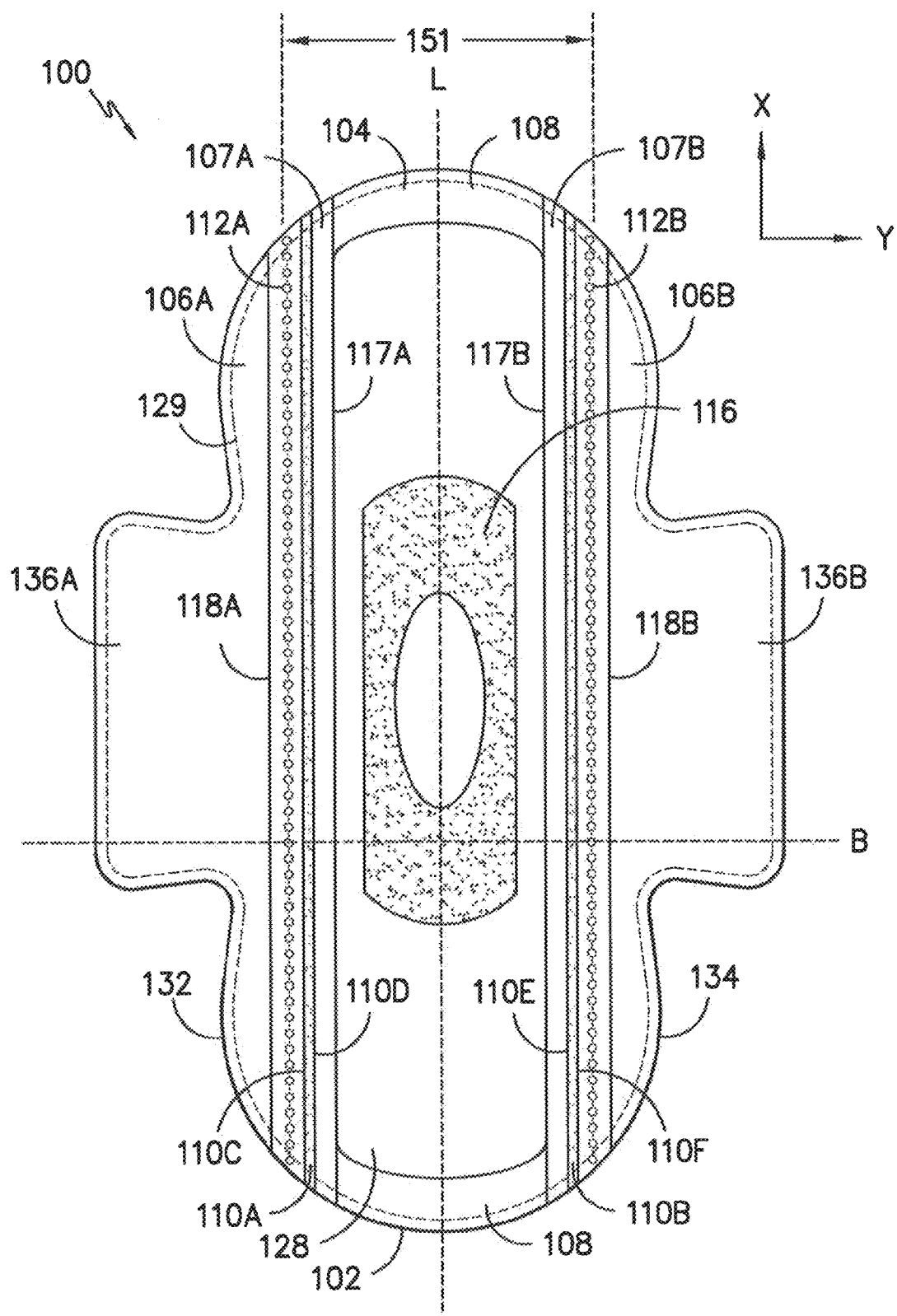
FIG. 1 is a top plan view of one embodiment of the absorbent article of the present invention.

As used herein the term "nonwoven fabric or web" refers to a web having a structure of individual fibers or threads which are interlaid, but not in an identifiable manner as in a knitted fabric. Nonwoven fabrics or webs have been formed from many processes such as for example, meltblowing processes, spunbonding processes, through-air bonded carded web (also known as BCW and TABCW) processes, etc. The basis weight of nonwoven webs may generally vary, such as from about 5 grams per square meter ("gsm") to 150 gsm, in some embodiments from about 10 gsm to about 125 gsm, and in some embodiments, from about 20 gsm to about 120 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki., et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 5,284,703 to Everhart, et al., and U.S. Pat. No. 5,350,624 to Georger, et al., each of which are incorporated herein in their entirety by reference thereto for all purposes.

As used herein, the term "decolorizing agent" refers to a chemistry, or chemical mechanisms which decolorizes or assists in the decolorizing of blood stains, such as for example, by either filtering or aggregating/binding blood cells from blood-containing fluids, lysing blood cells, causing alteration of the coloring agents from the blood cells, or otherwise chemically altering the perception of color of blood stains through color-changing mechanisms, such as through oxidation or bleaching mechanisms, catalytic oxidation or enzymatic reaction, with the final effect being a decrease or elimination of the red color intensity in certain portions of a feminine care absorbent article and/or fluid flowing out of a feminine care absorbent article. Such decolorizing agent effectively removes or alters the color of potentially staining fluid, so that fluid which unfortunately travels through or over/across the absorbent article to the article side edges, has less color for staining of garments or bedding, should there be an actual leak of fluid off of the article. By locking up menses coloring agents in particular article areas outside of the absorbent layers, additional absorption of the menses non-colored fluids (lower viscosity clear fluids), may occur throughout dedicated absorbent core areas. For the purposes of this disclosure, decolorizing agents are positioned either in or on decolorizing agent-containing carrier materials, which can be positioned lateral to the central longitudinal axis L of the absorbent article. Such decolorizing agent-containing layer or layers can be symmetrically positioned about the article (pad) central longitudinal axis L (or direction), and are located either along, directly along, or adjacent the side edges of the article (pad), such as the lateral side edges (the longitudinally directed side edges) or the end edges of the article. In one embodiment, such decolorizing agent-containing layer(s) are within 2 and 5 cm from the lateral most edge (the longitudinally directed side edges) of the article.

As used herein, the term "decolorizing agent carrier material" shall refer to a single layer material, a multiple-layered material structure, a laminate or laminae structure, or a combination thereof, which includes a decolorizing agent either in or on its material structure. The term decolorizing agent carrier layer may, in one embodiment, refer to two physically separated portions of the same layer that are within the same plane (especially when viewed along the depth axis) within an absorbent article, but which do not have any decolorizing agent disposed between them along the article transverse (y) axis or direction. Such two physically separated portions may be two, unconnected, discrete portions, such as separated strips of material in the same plane, or alternatively two portions which are separated at one location in the same plane (such as along a centrally positioned, insult-receiving portion/region of the pad), but which are connected in some fashion along, or adjacent the peripheral edges of the pad. Examples of laminate-type structures are described in U.S. Pat. Nos. 6,932,929 and 6,896,669 to Woltman, each of which are hereby incorporated by reference in its entirety. The articles to be described include at least one decolorizing agent carrier layer which desirably itself, includes a portion which is noncontinuous across the transverse axis of the absorbent article, such as a feminine care absorbent article. However, it is also to be understood that such physically separated portions may also be described as separate decolorizing agent carrier materials.

As used herein, the terms "superabsorbent polymer," "superabsorbent" or "SAP" shall be used interchangeably and shall mean polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAPs ability to absorb water is based in part on ionicity (a factor of the ionic concentration of the aqueous solution), and the SAPs functional polar groups that have an affinity for water. SAPs are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAPs may be present in absorbent articles in particle or fibrous form or as a coating on another material or fiber.

As used herein, the term "menses simulant" refers to a simulated menses fluid which may be used for testing feminine hygiene absorbent personal care articles. Such is described for example in U.S. Pat. No. 5,883,231 to Achter, et al. and in the publication by D. Guralski, Candee Krautkramer, Brian Lin, Jack Lindon, Teuta Elshani, Aneshia Ridenhour, entitled "A Biological Menses Simulant Using a "Batch" Homogenization Process", and published as Document IPCOM000198395D at ip.com, 6 Aug. 2010, each of which are hereby incorporated by reference in their entirety. For the purposes of this disclosure, menses simulant described in these publications was used for evaluation of article performance.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For the purposes of this application, like features will be represented by like numbers between the figures.

Generally speaking, the present disclosure is directed to an absorbent article containing a decolorizing region that is separated from an absorbent region of the absorbent article in the depth (z) direction. The absorbent article also includes a fluid barrier region for preventing the spread of fluids from the center of the absorbent article toward the edges of the absorbent article in the transverse (y) direction. The relationship between the decolorizing region and the fluid barrier region is such that the two regions are adjacent each other along the transverse (y) direction and are in the same plane or closely positioned planes in the depth (z) direction. The fluid barrier region can slow the flow of fluid towards the edges of the absorbent article so that the fluid is held in the decolorizing region for a sufficient time to be decolorized by the decolorizing agent.

For example, for a decolorizing agent chemistry to deliver optimal control over the fluid stain, the decolorizing agent chemistry is desirably integrated into a decolorizing system within the absorbent article. This system involves article constructions that control fluid access to the decolorizing agent chemistry in a decolorizing region. These constructions desirably funnel a limited amount of fluid to the decolorizing region, which can contain any suitable decolorizing agent chemistry, in a preferred direction and also separate or isolate the decolorizing agent chemistry from fluid that might come from other directions. It is to be understood that the two parts of the system (i.e., the fluid barrier region and the separating region) can be separate structures or can be integrated into a single structure.

The aforementioned funneling can limit the rate that fluid is delivered to the decolorizing region and can manage the fluid within the decolorizing region. This funnel can come from properly placed fluid barrier regions on or within the absorbent article. One example of a fluid barrier region can be a porous barrier such as an embossed region, discussed in more detail below. Examples of other forms of suitable fluid barrier regions can include a physical barrier such as a density gradient, a pore size gradient, a tortuosity gradient, or a topographical gradient or can include a wettability barrier such as a wettability gradient. Examples of such fluid barrier regions or structures are described in U.S. Pat. No. 3,397,697 to Rickard, U.S. Pat. No. 4,655,759 to Romans-Hess, et al., U.S. Pat. No. 6,703,538 to Lassen, et al., U.S. Pat. No. 6,171,682 to Raidel, et al., U.S. Pat. No. 5,575,785 to Gryskiewicz, et al., U.S. Pat. No. 5,810,798 to Finch, et al., U.S. Pat. No. 6,241,714 to Raidel, et al., U.S. Pat. No. 5,795,344 to Chappell, U.S. Pat. No. 6,667,424 to Hamilton, et al., and U.S. Pat. No. 7,388,123 to Cowell, et al., each of which are hereby incorporated by reference in their entirety.

Meanwhile, isolation can come from properly placed separation regions, which can be in the form of isolation structures disposed between the decolorizing region and the absorbent core. One example of such a separation region can be the placement of a layer between the decolorizing region and the absorbent core, where the layer limits direct fluid communication between the decolorizing region and the absorbent core. Other forms of separation regions can take the form of the strategic placement of an adhesive layer, a partial coating on the decolorizing region, a gap between the absorbent core and the decolorizing region, and partial or complete removal of the absorbent core. Various examples of separation regions/isolation structures can be found in U.S. Pat. No. 6,172,276 to Hetzler, et al., U.S. Pat. No. 6,673,982 to Chen, et al., U.S. Pat. No. 6,613,028 to Daley, et al., U.S. Pat. No. 6,348,253 to Daley, et al., and U.S. Pat. No. 6,534,149 to Daley, et al., and in U.S. Patent Publication Nos. 2003/0097105 to Chen, et al., 2003/0124336 to Keane, et al., 2004/0102752 to Chen, et al., and 2004/0127883 to Cowell, et al., each of which are hereby incorporated by reference in their entirety.

More specifically, in order to address the staining concerns perceived by consumers from potential absorbent article leakage, to reduce fears of embarrassment from garment or bedding stains resulting from such leakage, and to reduce the effort necessary in removing stains that may actually occur on garments or bedding, the invention provides a feminine care absorbent article with targeted decolorizing agents that can render menses stains and menses fluid a pale color, colorless, or nearly so, within select portions of an absorbent article, before the fluid leaves the article. Such decolorizing agents have the ability to render such stain or menses fluid a clear or pale yellow color, for example, so as to reduce potential staining risk to garments or bedding that may occur. Further, with reduced stain potential, any leakage that actually does occur will be easier to remove. Additionally, the invention contemplates the use of such decolorizing agents in combination with other structural barriers on or in an absorbent article, such as at least one encapsulated region and at least one embossed region, to impede menses flow to the side edges of the absorbent article and to reduce the visualization of article insult, when viewing the article from its body-facing surface. The present disclosure provides for a topsheet having side layers that include regions containing decolorizing agents and structural barriers, and, in some embodiments, additional regions containing decolorizing agents can be positioned between the topsheet and the absorbent core of the absorbent article. The structural barriers, such as the at least one encapsulated region and the at least one embossed region, can provide a wall to block or slow the spread of menses flow to the side edges of the absorbent article, which can, in turn, provide the decolorizing agent with sufficient contact time or dwell time to decolorize an insult of menses fluid that has spread to the side layers of the topsheet of the absorbent article.

Figure 2:
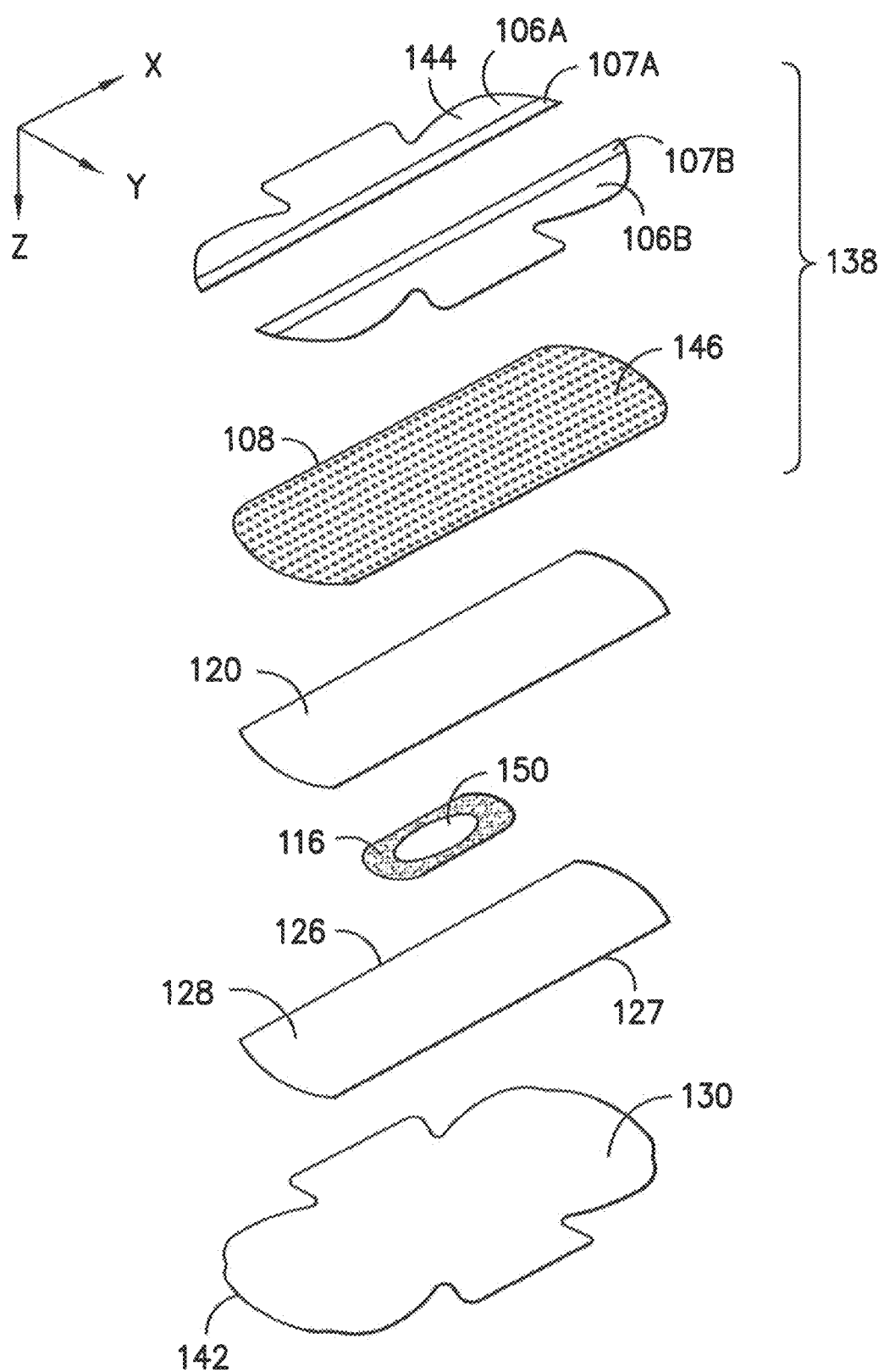
FIG. 2 is an exploded perspective view of FIG. 1.

FIGS. 1 and 2 illustrate a top plan view and exploded perspective view respectively, of one embodiment of an absorbent article of the present invention, in the form of a feminine care absorbent article. The absorbent article has a longitudinal (x) axis, a transverse (y) axis, and a depth (z) axis, which is the direction normal to the plane of the pad layers. The feminine care absorbent article 100, having a distal end 102 and a proximal end 104, has side wings 136A and 136B extending out at the longitudinally directed first and second side edges 132 and 134 of the absorbent article. As shown in FIG. 2, the feminine care absorbent article 100 also contains a liquid impermeable, garment-facing backsheet 130 and a liquid permeable, body-facing topsheet 138 that includes a central layer 108 that is positioned adjacent the first and second opposing side layers 106A and 106B, at least one of which can include at least one encapsulated region 107A or 107B, respectively. Further, the backsheet 130 and the topsheet 138 sandwich at least one absorbent core 128.

Additionally, although not shown, the topsheet 138 may surround the absorbent core 128 so that it completely encases the absorbent core layer 128 and/or backsheet layer 130. Alternatively and as shown in FIGS. 1 and 2, the topsheet 138 and the backsheet 130 may both extend beyond the outermost peripheral edges 126 and 127 of the absorbent core 128 and be peripherally joined together, either entirely or partially, using known attachment techniques to form a sealed region 129. Typically, the topsheet 138 and the backsheet 130 can be joined by adhesive bonding, ultrasonic bonding, or any other suitable joining method known in the art. The feminine care absorbent article 100 may take on various geometries but will generally have opposite lateral side edges 132, 134 (in the product longitudinal direction) and longitudinal distal and proximal ends 102, 104. Each of these layers, along with additional optional layers, is discussed in more detail below.

Topsheet

The topsheet layer 138 is generally designed to contact the body of the wearer and is liquid-permeable. The liquid permeable topsheet layer 138 defines a body-facing surface 144 of the absorbent article 100 that may directly contact the body of the wearer and receive bodily exudates. The topsheet 138 is desirably provided for comfort and conformability and functions to direct bodily exudates away from the body of a user, through its structure and towards the absorbent core 128. The topsheet 138 desirably retains little or no liquid in its structure, so that it provides a relatively comfortable and non-irritating surface next to the tissues within the vestibule of a female wearer.

Central Layer

The central layer 108 of the topsheet 138 can be constructed of any woven, nonwoven or sheet material which is easily penetrated by bodily exudates which may contact the body-facing surface 144 of the absorbent article 100. Examples of suitable topsheet materials include natural fiber webs (such as cotton), rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated films and net materials can also be used, as can laminates of/or combinations of these materials. A specific example of a suitable central topsheet layer material is a bonded carded web (BCW) made of polypropylene and polyethylene such as that obtainable from Sandler Corporation, Germany. U.S. Pat. No. 4,801,494 to Datta, et al. and U.S. Pat. No. 4,908,026 to Sukiennik, et al., and WO 2009/062998 to Texol teach various other topsheet materials that may be used in the present invention, each of which is hereby incorporated by reference in its entirety. The central layer 108 may contain a plurality of apertures 146 formed therethrough to permit body fluid to pass more readily into the absorbent core 128. The apertures 146 may be randomly or uniformly arranged throughout the central layer 108 of the topsheet 138, or they may be located only in a narrow longitudinal band or strip arranged along the length of the feminine care absorbent article 100, such as down the longitudinal (x) axis of the article. The size, shape, diameter and number of apertures may be varied to suit an article's particular needs. In another embodiment, the central layer 108 can have a basis weight ranging from about 10 gsm to about 120 gsm. For instance, in one embodiment, the central layer 108 can be constructed from a through air bonded carded web (TABCW) having a basis weight ranging from about 15 gsm to about 100 gsm. In another embodiment, the central layer 108 can be constructed from a TABCW having a basis weight ranging from about 20 gsm to about 50 gsm, such as a TABCW that is readily available from nonwoven material manufacturers, such as Xiamen Yanjan Industry, Beijing DaYuan Nonwoven Fabrics and others. Regardless of the material from which the central layer 108 is formed, it can extend in a longitudinal direction and be positioned adjacent a first side layer 106A and a second side layer 106B such that the central layer 108 includes a portion 115 that is exposed and bordered by the first side layer 106A and the second side layer 106B, which are discussed in more detail below.

Side Layers

In addition to the central layer 108 discussed above, the topsheet 138 further includes side layers 106A and 106B, as shown in FIGS. 1-10, which can be positioned adjacent and which can overlap with the central layer 108 on opposing sides of the absorbent article 100 in the transverse (y) direction. For instance, with specific reference to FIGS. 1 and 2, in one embodiment, the central layer 108 can be positioned along the central longitudinal axis L of the topsheet 138, while the side layers 106A and 106B extend out therefrom toward first side edge 132 and second side edge 134. Examples of such a construction are generally described in U.S. Pat. No. 5,961,505 to Coe, U.S. Pat. No. 5,415,640 to Kirby, and U.S. Pat. No. 6,117,523 to Sugahara, each of which is incorporated by reference herein in its entirety.

The side layers 106A and 106B of the topsheet 138 can be constructed of any suitable nonwoven, woven, or film sheet materials that can be different from or the same as the material used to form the central layer 108. The selection of the particular materials for the side layers 106A and 106B can vary based on the overall desired attributes of the topsheet 138. For instance, various nonwoven fabrics or webs such as meltblown webs, spunbond webs, or through-air bonded carded webs (TABCW) can be utilized in the side layers 106A and 106B. In one embodiment, it may be desired to have at least a partially hydrophilic material as the central layer 108, while inherently hydrophobic barrier-type materials or barrier-type materials treated with a hydrophobic coating can be used as the side layers 106A and 106B to prevent leakage and increase a sensation of dryness. Thus, the side layers 106A and 106B can be formed from a TABCW having a basis weight ranging from about 10 gsm to about 75 gsm, such as from about 15 gsm to about 50 gsm, such as from about 20 gsm to about 30 gsm. It should also be understood that, although not shown, the TABCW, or any other material used for the side layers 106A and 106B, can have incorporated within it a masking colorant, such as titanium dioxide particles, to increase the opacity or white pigment of the side layers 106A and 106B. Such masking colorants can enable the side layers 106A and 106B to mask stains that may be created by the spread of menses fluid. Printing of other colors and graphics can also be present on the side layers 106A and 106B, although not shown, to further mask any stains. At least one of the side layers 106A and 106B may be either adhesively, thermally, ultrasonically, or otherwise bonded to the central layer 138 along an encapsulated region 107A or 107B (discussed in greater detail below) of one of the side layers 106A or 106B. In addition, a decolorizing agent carrier material 110A or 110B containing or carrying a decolorizing agent 109 can be placed on a surface of at least one of the side layers 106A or 106B, after which the resulting laminate 124A or 124B, including the side layer 106A or 106B, decolorizing agent carrier material 110A or 110B, and decolorizing agent 109, can be folded at least once along a fold axis 117A or 117B located toward the longitudinal centerline of the absorbent article 100 (discussed in more detail below and as shown in FIGS. 1 and 3-10). Further, as shown in FIGS. 3-10, an adhesive 103 can be used to join the central layer 108 with the side layers 106A and 106B to form the topsheet 138. Moreover, although not shown, it is to be understood that the aforementioned side layers and decolorizing agent carrier material/decolorizing agent features may run along the distal end 102 and proximal end 104 of the absorbent article in the transverse (y) axis direction, although the figures show the side layers and decolorizing agent carrier material/decolorizing agent features as running along the longitudinal (x) axis direction.

Decolorizing Agent Carrier Material and Decolorizing Agent

Before adhering, bonding, or otherwise connecting the side layers 106A and 106B to the central layer 108 to form the topsheet 138, a decolorizing agent carrier material 110A or 110B that has been treated with a decolorizing agent 109, as shown in FIGS. 3-10 and mentioned above, can be joined to a portion of the side layer 106A or 106B to form a laminate 124A or 124B, at least one of which can be folded at least once, such as along fold axis 117A or 117B, to form a fold 105A or 105B that defines an encapsulated region 107A or 107B.

The decolorizing agent carrier material 110A or 110B may be selected from foam materials, sponge-like network materials, nonwoven materials such as tissue layers, woven materials, airlaid materials, coform materials, uncreped through air dried materials, etc. In one embodiment, when the nonwoven decolorizing agent carrier material is a nonwoven material, such as a tissue, it is desirable for such basis weight to be between about 10 gsm and about 150 gsm. Meanwhile, for foam-type carrier materials, it is desirable for such basis weight to be between about 100 gsm and about 200 gsm.

In some embodiments, the decolorizing agent carrier material 110A or 110B and/or the decolorizing agent 109 can be disposed between or located inside the peripheral edges 126 and 127 of the absorbent core 128 in the transverse (y) direction when viewed from the body facing surface 144. In other words, when a cross section of the transverse (y) direction and depth (z) direction is taken of the absorbent article, as shown in FIGS. 3-10 and 13-20, the decolorizing agent carrier material 110A or 110B and/or the decolorizing agent 109 can be positioned above the absorbent core 128 and between the boundaries formed by the peripheral edges 126 and 127 of the absorbent core 128 in the depth (z) direction. Further, although not shown, it is to be understood that the decolorizing agent carrier materials 110A and/or 110B and/or decolorizing agent 109 may extend beyond the peripheral edges 126 and 127 of the absorbent core layer(s) and toward side edges 132 and 134 in the transverse (y) direction in some embodiments when viewed from the body-facing surface 144. Further, although FIG. 1 shows the decolorizing agent carrier materials 110A and 110B extending continuously from the distal end 102 to the proximal end 104 of the absorbent article in the longitudinal (x) direction, it is to be understood that, in some embodiments, although not shown, the decolorizing agent carrier materials 110A and 110B may not extend all the way to the distal end 102 and proximal end 104. Further, it is to be understood that the decolorizing agent carrier materials 110A and 110B may be discontinuously disposed along the length of the absorbent article in the longitudinal (x) direction. In addition, it is also to be understood that although the decolorizing agent carrier material 110A is defined in the transverse (y) direction by outer edge 110C and inner edge 110D that appear as straight, parallel lines, in some embodiments (not shown), outer edge 110C can be a curved line, such as a curved line formed by die cutting, to draw attention to the stain-spreading barrier created by the decolorizing agent carrier material 110A due to filtration and/or the decolorizing agent 109. Likewise, it is also to be understood that although the decolorizing agent carrier material 110B is defined in the transverse (y) direction by outer edge 110F and inner edge 110E that appear as straight, parallel lines, in some embodiments (not shown), outer edge 110F can be a curved line, such as a curved line formed by die cutting, to draw attention to the stain-spreading barrier created by the decolorizing agent carrier material 110A due to capillary action/filtration and/or the decolorizing agent 109.

In some embodiments, such as the embodiment of FIGS. 3-4 and 7-8, the decolorizing agent carrier material 110A or 110B can be a meltblown microfiber (MBMF) material. In other embodiments, such as the embodiment of FIGS. 5-6, the decolorizing agent carrier material 110A or 110B can be a TABCW, such as the TABCW discussed above. Regardless of the particular material selected for the decolorizing agent carrier materials 110A and 110B, it should also be understood that, although not shown, such material can have incorporated within it a masking colorant, such as titanium dioxide particles, to increase the opacity or white pigment of the decolorizing agent carrier materials 110A and 110B. Such masking colorants can enable the decolorizing agent carrier materials 110A and 110B to mask stains that may be created by the spread of menses fluid. Printing of other colors and graphics can also be present on the decolorizing agent carrier materials 110A and 110B, although not shown, to further mask any stains.

When the decolorizing agent carrier material 110A or 110B is MBMF, such as a polypropylene microfiber material, the basis weight of the decolorizing agent carrier material can range from about 10 gsm to about 100 gsm, such as from about 20 gsm to about 50 gsm, such as from about 25 gsm to about 40 gsm. Further, the MBMF can have a fiber size ranging from about 1 micron to about 10 microns in diameter. Such a material is available from Yuhan-Kimberly Ltd., Seoul, Korea.

Because the aforementioned MBMF materials are inherently hydrophobic, they can be treated with wetting agents for adequate handling of aqueous fluids such as menses. However, in some embodiments, the MBMF or other decolorizing agent carrier material can be hydrophobic, at least on one side. Examples of such wetting agents include surface active agents (or surfactants) having a hydrophilic lipophilic balance (HLB) of at least about 6, such as between about 7 and about 18. Definitions of "surfactant" and "HLB scale" can be found in textbook "Introduction to Colloid and Surface Chemistry", by Duncan J. Shaw, $4^{th}$ edition, 1992, published by Butterworth-Heinemann, Ltd. A variety of surfactants can be used and include those that are anionic, cationic, or neutral from a charge standpoint. Mixtures of surfactants and other wetting agents can also be used. Typical wetting agent add-on can range from about 0.1 wt. % to about 10 wt. %, such as from about 0.2 wt. % to about 5 wt. % based on the weight of the substrate (i.e. decolorizing agent carrier material 110A or 110B). However, it should be understood that add-on levels higher than about 10 wt. % can also be used. These wetting agents can have an effect of moving aqueous fluids through a porous media such as the aforementioned MBMF. It has been found that only certain wetting agents can aid in decolorizing fluids such as menses fluid. As such, the extent of decolorizing can depend on the type of wetting agent selected. The decolorizing agent 109 on such a decolorizing agent carrier layer 110A or 110B can be a polyethylene glycol (PEG), which can applied via slot coating or any other suitable method (discussed below) in an amount ranging from about 10 gsm to about 30 gsm, although other decolorizing agents can also be used and are discussed in more detail below. One PEG that can be used is PEG 8000 Carbowax Sentry. As shown in FIGS. 1-10, the two longitudinally directed side layers 106A and 106B of the topsheet 138 are shown as separate sections, with a central layer 108 that is adjacent each of the side layers 106A and 106B. For instance, the central layer 108 can be disposed between the side layers 106A and 106B, the central layer 108 being free of the aforementioned decolorizing agent carrier material 110 and decolorizing agent 109.

The decolorizing agents that can be used in conjunction with the structural embodiments described herein include a wide array of chemistries. While any known decolorizing agents may be used, the decolorizing agents can generally include one or more decolorizing agents selected from the following categories of chemistries.

In one embodiment of the invention, the decolorizing agent can be a menses filtration chemistry, i.e., an agent that can precipitate, coagulate, phase separate components, or otherwise demonstrate an affinity to the red components of menses. Such a chemistry may be applied/treated on one or more of the layers of the feminine hygiene absorbent article 100. It has been found that when menses insults the treated material, the red component of the menses, composed of the protein hemoglobin, is rendered insoluble in an aggregate form, and is retained by the layer of the article, while only a clear or slightly colored solution that is relatively innocuous to staining, leaches from the insulted area. Therefore, any side leakage from a pad, or rewet (that is, fluid flowing back out of the pad from the topsheet surface), demonstrates a clear appearance or reduced coloration.

Such a menses filtration chemistry is exemplified by relatively high molecular weight polyethylene glycols (PEG), polyethylene oxides (PEO), and methoxypolyethylene glycols (MPEG), with PEGs being most desirable. It has been found that a broad range of high average molecular weight PEGs, PEOs and MPEGs, and add-on levels can be used with the invention. In particular, higher molecular weight PEGs have been seen to have stronger hemoglobin precipitation effect, that is, the concentration of PEG required to induce hemoglobin precipitation decreases as higher molecular weight PEGs are used. However, since the solubility of PEGs also decreases with higher molecular weights, this results in a slower filtration effect. It has therefore been found that in one embodiment, polyethylene glycols or PEGs and polyethylene oxides or PEOs having average molecular weights of between about 300 and about 2,000,000, such as between about 500 and about 2,000,000, such as between about 1,000 and about 1,000,000, such as between about 1,000 and about 400,000, such as between about 1,000 and about 100,000, such as between about 3,000 and about 100,000 are desirable for use with this invention. In another embodiment, PEGs or PEOs having average molecular weights between about 3,000 and about 35,000 can be used. As the ethylene oxide chain impacts functionality of the invention, PEG variants with different functional groups on each end can also be acceptable for use in the absorbent article of the present disclosure. Linear as well as branched forms can also be used in the absorbent article of the present disclosure. For example, higher molecular weight methoxypolyethylene glycols or MPEGs similarly have such an effect that is MPEGs having a molecular weight greater than or equal to about 750. These ranges demonstrated noticeable discoloration of menses from surrounding fluid. Still in a further embodiment, PEGs having average molecular weights of between about 4,000 and about 12,000 can be used. Suitable PEG and PEO materials are available from the Dow Chemical Company under the trade name CARBOWAX and CARBOWAX SENTRY, from Sigma Aldrich, and Acros Organics. Finally, other chemical derivatives, such as Cetiol-HE will have similar effects as PEG and thus are contemplated to be within the scope of the invention.

The relative percentages of add-on, and add-on level in gram per square meter (gsm) or in weight percent (wt. %) of the composition with respect to a dimension of the decolorizing agent carrier material (area or weight) may vary to achieve the desired level of decolorizing. The "add-on level percentage with respect to weight" is determined by subtracting the weight of the untreated carrier material from the weight of the treated carrier material (after any optional drying steps), dividing this calculated weight by the weight of the untreated carrier material, and then multiplying by 100% to produce a weight percent. In some embodiments involving PEG, PEO, and MPEG decolorizing agent chemistry, the add-on level of the decolorizing agents can be at least about 15 wt. %, such as at least about 25 wt. %. For instance the add-on level can range from about 15 wt. % to about 190 wt. %, or from about 50 wt. % to about 200 wt. %.

The add-on level in gsm of the decolorizing agent can also be expressed as the actual added dried weight (in grams) to the same area of the initial decolorizing agent carrier material. In some embodiments, the add-on level can range from about 5 gsm to about 150 gsm, such as from about 5 gsm to about 100 gsm, such as from about 4 gsm to 40 about gsm, such as from about 60 gsm to about 100 gsm. In particular, for a PEG having a molecular weight of 8,000, treatment at about 5 gsm to about 40 gsm or alternatively from about 50 gsm to about 100 gsm add-on level is desirable.

Since the higher molecular weight polyethylene glycols (PEGs) are solids, they can be melted and applied onto the decolorizing agent carrier material by slot die coating ("slot coating process") or spray applications. Alternatively, PEGs may be placed in solvents such as water or alcohol and applied by saturation, spraying, kiss roll, dipping or various printing methods.

Such application of the PEG or other decolorizing agent to the decolorizing agent carrier material may be uniform or non-uniform. Since higher add-on levels of such chemistries have a higher decolorizing effect, but also impact absorbency, it is can be desirable to place such decolorizing agents in predominantly nonabsorbent layers, as well as within the periphery of, yet disposed above, the absorbent layers.

Additional menses filtration chemistry that can be used in conjunction with the structural invention include surface active agents ("surfactants") such as those that are based on polyether siloxane chemistry. Examples of polyether siloxanes, also referred to as dimethicone copolyols, include but are not limited to MASIL SF 19, available from Emerald Performance Materials, LLC, Cheyenne, Wyo., and Dow Corning 193C Fluid ("DC193C") and Dow Corning Q2-5211 Superwetting Agent ("Q2-5211"), both available from Dow Corning, Midland, Mich. Other surfactants that can be used include ethoxylated fatty esters such as hydrogenated ethoxylated castor oil. Another family of surfactants that may be used include those in the alkyl polyglycoside ("APG") category, such as those described in U.S. Pat. No. 6,060,636 to Yahiaoui, et al. which is hereby incorporated by reference thereto in its entirety. An example of such surfactants include Glucopon 220 UP and Standapol 215 UP, available from Cognis Corp. of Cincinnati, Ohio Another example of a surfactant that may be used as a decolorizing agent includes, Cirrasol PP 862 (formerly known Ahcovel Base-N 62) from Croda, Inc.

As with the PEGs, PEOs, and derivatives thereof, such as methyl end-capped PEGs (or MPEGs), it has been found that a broad range of surfactants and wetting agent add-on levels may be used in conjunction with the invention, as described above.

It has also been found that denser or variable density fibrous layer materials may further enhance the filtration effects of the chemical filtration agent materials as well. In particular, it has been found that the substrate (e.g., carrier material) and decolorizing agent chemistry can be manipulated to create a synergistic filtration effect. It is observed that two factors of the base carrier material can contribute to the filtration effect, the first being the pore size of the substrate, and the second being the wicking capability of the material. Therefore several materials may be desirable embodiments for use as the decolorizing agent carrier material. For this reason, the hydrophilically treated meltblown microfiber substrate, discussed in detail above, can be used due to its pore size, bulk, and wicking abilities. Another material that can be used is a TABCW if a softer material is desired. Further, it should be understood that multiple layers of PEG-treated materials, such as MBMF, TABCW, airlaid materials, etc., can be bonded together in a staggered format to also enhance the filtration effect. By staggered, it is meant that a piece of material is joined to another with some overlap, but also with some spacing between layers. The staggered nonwoven increases the flow path of the menses in the same manner of a high wicking/highly porous substrate, thereby increasing the filtration efficiency of the PEG. Such a combination can enhance the stain barrier function of the material, thereby limiting the visual stain spread to a certain region, allowing clear or almost clear fluid only, to pass out of the denser substrate area. In further alternative embodiments of the article, several decolorizing-agent containing layers may be separated by physical gaps or spaces, or one or more layers within the article, or alternatively, placed one upon the other (immediately adjacent one another in the depth (z) direction), placed adjacent each other in the transverse (y) direction, or placed adjacent in the longitudinal (x) direction. Such separation would assist in the lateral and longitudinal wicking/ distribution of the menses stain in the article.

In order to test the PEG chemistry for its intended usage, the following experiments were conducted:

PEG Experimental Examples

The general procedure for producing high, average, molecular weight PEG-treated and related chemistry, substrates is detailed below.

Different average, molecular weight-sized PEGs were applied to nonwoven materials by soaking the nonwoven samples and subsequently air-drying, with 5%, 10%, 15%, 20%, 25%, and 30% (w/w) PEG solution in water on a 60 gsm latex-bonded pulp-based, single-layered airlaid substrate (Sambo, Korea). The add-on was from 0.37 grams to 0.40 grams of PEG. PEGs were obtained from Dow Chemicals, in granular or flake form under the trade name CARBOWAX, from Sigma Aldrich, and from Acros Organics. First the PEG was dissolved in distilled water at 20% concentration. The airlaid was dipped in the PEG solution, excess liquid was removed by suspending it in mid-air for 15 minutes and then dried in an oven set to 80° C. in a flat state for 2 hours. Alternatively, the sample was allowed to air dry for two days. The obtained and treated sheets were tested to observe the discoloration by filtration on the sheets. For the purposes of these experiments, filtration of the sheets was conducted by dropping 0.1 grams to 0.3 grams of menses simulant, or alternatively 200 microliters (uL), dropwise from a pipette onto the sheets. The sheets were then examined to see if there was a discoloration gap or zone in the stain as it wicked on the substrate which resulted from the plasma (clear fluid) separating from the red blood cells or hemoglobin. For the purposes of these experiments, add-on was calculated as the percentage of basis weight of PEG added divided by the basis weight of the base material.

3,015-3,685 average molecular weight PEG (Sigma Aldrich) treated sheets showed a partial decolorized gap (1 mm) from menses colored regions, from 90% add-on level up to 190% (approximately 2 mm). Higher add on level of PEG gave wider discoloration gap (1-2 mm) but no more than 2 mm gap, and became more stiff on the sheet, the higher level of add-on being used.

7,000-9,000 average molecular weight PEG (Acros Organic) treated sheet showed a partial decolorized gap (less than 1 mm) from menses colored regions, from 60% add-on level up to 190% add-on level. Higher add on level of PEG showed wider discoloration gap (1~2 mm) but no more than 2 mm gap, and became more stiff on the sheet, the higher level of add-on being used.

16,000-24,000 average molecular weight PEG (Sigma Aldrich) treated sheet showed a partial decolorized gap from menses colored regions, from 60% add on level up to 190%. Higher add on level of PEG showed wider discoloration gap (1~2 mm) but no more than 2 mm gap, and became more stiff of the sheet, the higher level of add-on being used.

35,000 average molecular weight PEG (Sigma Aldrich) treated sheet showed a partial decolorized gap from menses colored regions, from 60% add-on level up to 190% add-on level. Higher add on level showed wider discoloration gap (1~2 mm) but no more than 2 mm gap, and became more stiff on the sheet, the higher the level of add-on being used.

In the tests with different molecular weight PEGs, the higher molecular weight PEGs required less add on amount for the same discoloration of menses simulant, but it was noted that for PEGs having a molecular weight above 8,000, the differences were insignificant in filtration observation. It was also noted that the solubility of PEG in aqueous medium decreased significantly with increased molecular weight. As more time was needed for the PEG to solubilize, the discoloration gap was reduced.

Meltblown micro fiber sheets (MBMF of polypropylene) were also used in the experiments, having a basis weight of 50 gsm. It should be noted however, that MBMF webs of 20 gsm, 30 gsm, and 60 gsm are also available. The sheets were supplied by Yuhan-Kimberly Ltd. Korea, and also available from FiberTex, Malaysia. The sheets were hydrophilically treated by either Aerosol GPG of Cytec, or alternatively Ahcovel Base N-62.

In particular, a 50 gsm hydrophilically treated MBMF sheet was treated with 3,015-3,685 average molecular weight PEG and 7,000-9,000 average molecular weight PEG by soaking and air-drying with 30% (w/w) PEG solution in water, which gave 130% or 106% add-on amount on the MBMF respectively. These sheets were tested for discoloration by filtration of the menses simulant on the sheets. A resulting higher discoloration gap (3-mm) was demonstrated. Additionally, the resulting meltblown material appeared softer than the pulp-based airlaid.

MPEG was also tested for its ability to decolorize menses. In particular, the same general testing procedures were employed. MPEG was obtained from Dow Chemical having an average molecular weight of about 750. A 15 wt. % MPEG solution was prepared. The airlaid or MBMF carrier materials were dipped in the solution and dried in the air. A few drops of simulant (1-3 drops) were placed on the MPEG-treated material and after a couple of minutes, clear fluid was observed along the peripheral areas around the simulant in the material.

In other embodiments, other chemistries can be used as the decolorizing agent(s) of the present disclosure. In particular, the decolorizing agent for a decolorizing agent carrier material can be selected from the group of trichloroacetic acid, ammonium sulfate and acrylate polymers (carbomers) or combinations thereof, with the optional addition of non-ammonium sulfate salts. Examples of such an acrylate polymer that is desirable includes carbomer available through Lubrizol, Ohio and Spectrum Chemicals of New Jersey and California. Carbomers from other vendors and suppliers may also be used. Specific examples of desirable carbomers include Carbopol ETD 2020, Carbopol Ultrez 21, Carbopol 980 NF, and Carbopol 1342 NF of Lubrizol. Examples of salts to be used with such acrylate polymer include sodium chloride, magnesium chloride, potassium chloride and ammonium sulfate. In one embodiment, an acceptable range of such a combination would be between about 0.1% to about 1% carbomer and between about 4% salt and about 20% salt. The decolorizing agent carrier material can be loaded with the carbomer-based decolorizing agent and then positioned, for instance, within the side layers of the topsheet of the absorbent article. In one embodiment, the carbomer-based decolorizing agent can be applied to a carrier material using a dip and squeeze or spray method and in add-on levels/amounts of carbomer between about 9 gsm and about 33 gsm, NaCl between about 17 gsm and about 78 gsm, and ammonium sulfate of between about 16 gsm and about 310 gsm.

In a further embodiment of the present disclosure, a zinc-oxide suspension in a combination of water and surfactants has been found to be a useful decolorizing agent. It has been found that for such a zinc-oxide system to be successful, it is desirable for acidifying agents to be present to keep the relative pH at a desired level of between about 3 and about 6. Additionally, zinc-oxide must be stably bound. As a result, in one embodiment where zinc-oxide is used as a decolorizing agent, the mixture includes zinc-oxide particles, a surfactant to disperse the zinc-oxide, an acidifying agent, a binder for attaching such zinc-oxide to a decolorizing agent carrier material, and a solvent. Such a mixture can be applied to a decolorizing agent carrier material in one step, rather than through a multistep process. In one embodiment, the zinc-oxide can be present in an amount ranging from about 0.1 wt. % to about 20 wt. %, such as in an amount ranging from about 0.5 wt. % to about 10 wt. %; the surfactant can be present in an amount ranging from about 0.1 wt. % to about 20 wt. %, such as in an amount ranging from about 0.5 wt. % to about 10 wt. %; an acidifying agent can be present to create a pH range of between about 3 and about 6; and a binder can be present in an amount ranging from about 0.1 wt. % to about 10 wt. %, such as in an amount ranging from about 0.5 wt. % to about 5 wt. %. An example of such zinc-oxide particles includes Solaveil CZ-300 from Croda (Edison, N.J.), zinc-oxide from NanoScale Materials, Inc., Manhattan, Kans. Examples of such surfactants include DC 193 C from Dow Corning (Midland, Mich.) and Ahcovel Base N-62 from ICI. In one embodiment, superwetting agents are more desirable, such as a siloxane polyether. Examples of such acidifying agents include lactic acid from Sigma Aldrich (Milwaukee, Wis.). Examples of such binders include Chitosan such as Hydagen HCMF from Cognis (Cincinnati, Ohio). Desirably, such mixture has an add-on of between about 0.2 wt. % and about 20 wt. % to a variety of decolorizing agent carrier materials, including microfiber meltblown fibers, TABCWs, and other nonwovens and laminates having similar capillary structures. Such a zinc-oxide decolorizing agent can also include other functional chemistries as desired, such as for example, preservatives, anti-oxidants, scents, pigments and anti-microbial agents. Further, rather than zinc-oxide, other metal oxides such as silica can be used, also at lower pH environments.

Regardless of the decolorizing agent utilized and as mentioned briefly above, a variety of techniques may be used for applying the decolorizing agent to a suitable decolorizing agent carrier material. For instance, the decolorizing agent may be applied using rotogravure or gravure printing, either direct or indirect (offset). Gravure printing encompasses several well-known engraving techniques, such as mechanical engraving, acid-etch engraving, electronic engraving and ceramic laser engraving. Such printing techniques provide excellent control of the agent composition distribution and transfer rate. Suitable gravure printing techniques are described in U.S. Pat. No. 6,231,719 to Garvey, et al., which is incorporated herein in its entirety by reference thereto for all purposes. Moreover, besides gravure printing, it should be understood that other printing techniques, such as flexographic printing, ink-jet printing, laser printing, thermal ribbon printing, piston printing, spray printing, etc. may also be used to apply the decolorizing agent to the decolorizing agent carrier material. Still other suitable application techniques may include bar, roll, knife, curtain, spray, slot-die, dip-coating, drop-coating, extrusion, stencil application, etc. Such techniques are well known to those skilled in the art. For example, in one embodiment, the decolorizing agent can be applied to the decolorizing agent carrier material in a continuous line by slot-coating. The decolorizing agent can thus be applied over the entire decolorizing agent carrier material or over a lesser area, such as an area that is from about 25% to about 75%, such as from about 30% to about 60%, such as from about 35% to about 55%, of the surface area of at least one side surface (e.g. the upper surface, the lower surface, or both) of the entire decolorizing agent carrier material surface area. Further, it should be understood that the decolorizing agent may be present on one or both of the upper surface and lower surface of the decolorizing agent carrier material and/or embedded throughout the decolorizing agent carrier material depending on how the decolorizing agent is applied to the decolorizing agent carrier material. However, it is also to be understood that the decolorizing agent carrier material itself, without a decolorizing agent applied thereto, can function as a decolorizing layer due to the rapid capillary action properties of the material, such as when MBMF is used as the decolorizing agent carrier material.

Figure 11:
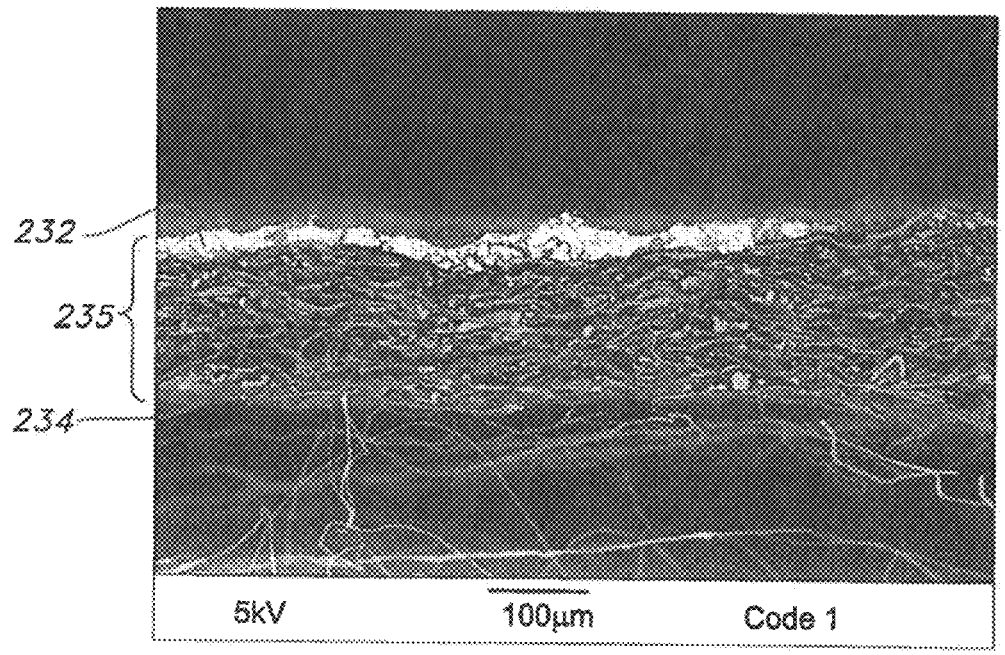
FIG. 11 is a microscopy image of a top surface coated decolorizing agent carrier material of the present disclosure, in the form of a coated meltblown nonwoven layer.
Figure 12:
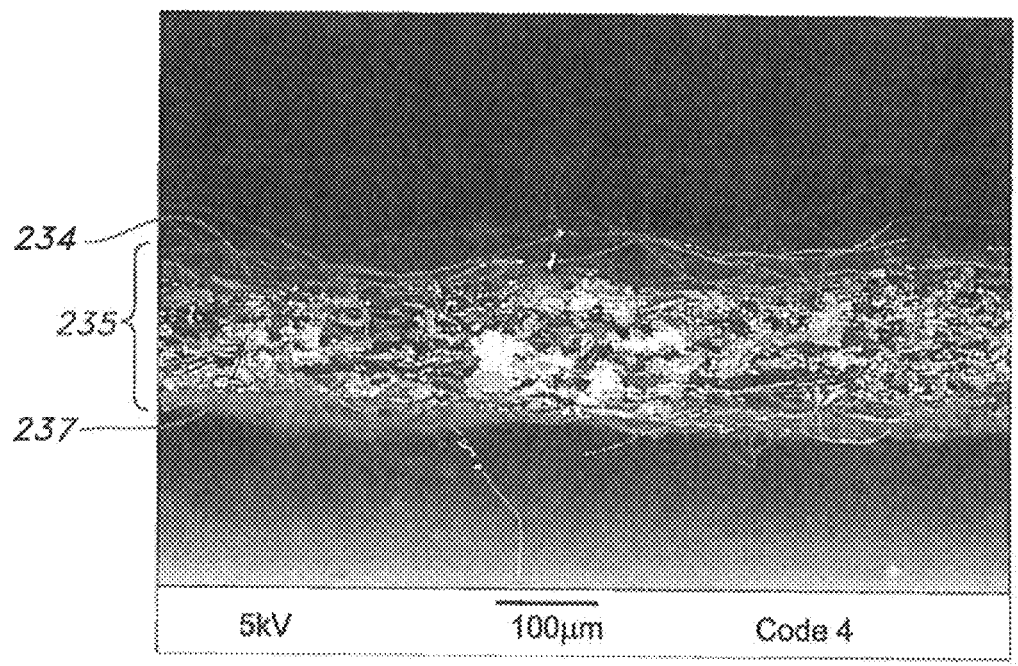
FIG. 12 is a microscopy image of an impregnated decolorizing agent carrier material of the present disclosure, in the form of a treated meltblown nonwoven layer.

For instance, as can be seen in the microscopy images in FIGS. 11 and 12 showing such PEG applications, following slot coat application onto a meltblown decolorizing agent-carrier layer 234, the PEG decolorizing agent 232 primarily sits along the topsheet-layer facing surface of the meltblown layer, without significant penetration into the meltblown fibrous layer of the PEG/meltblown combination 235. Following the alternative application using immersion and drip methodology (including PEG in solution), the PEG, 237 has penetrated the meltblown fibrous web 234 of the overall PEG/meltblown combination 235.

Regardless of the method of application, the carrier material may sometimes be dried at a certain temperature to drive any solvent from the decolorizing composition. For example, the treated substrate may be heated to a temperature of at least about 80° C., in some embodiments at least about 120° C., and in some embodiments, at least about 150° C. Generally, the required drying temperature is dependent on level of solvent (e.g. water) present on the substrate following treatment and on the line speed during a typical continuous production process. In other words, a temperature is applied for a dwell time that is necessary to flash off the solvent. By minimizing the amount of solvent in the decolorizing agent composition, a larger amount of agent may be available for contacting bodily exudates, thereby enhancing its ability to decolorize hemoglobin or other colored substances contained in menses exudates.

Decolorizing Agent Carrier Material and Embossing in the Topsheet

Figure 3:
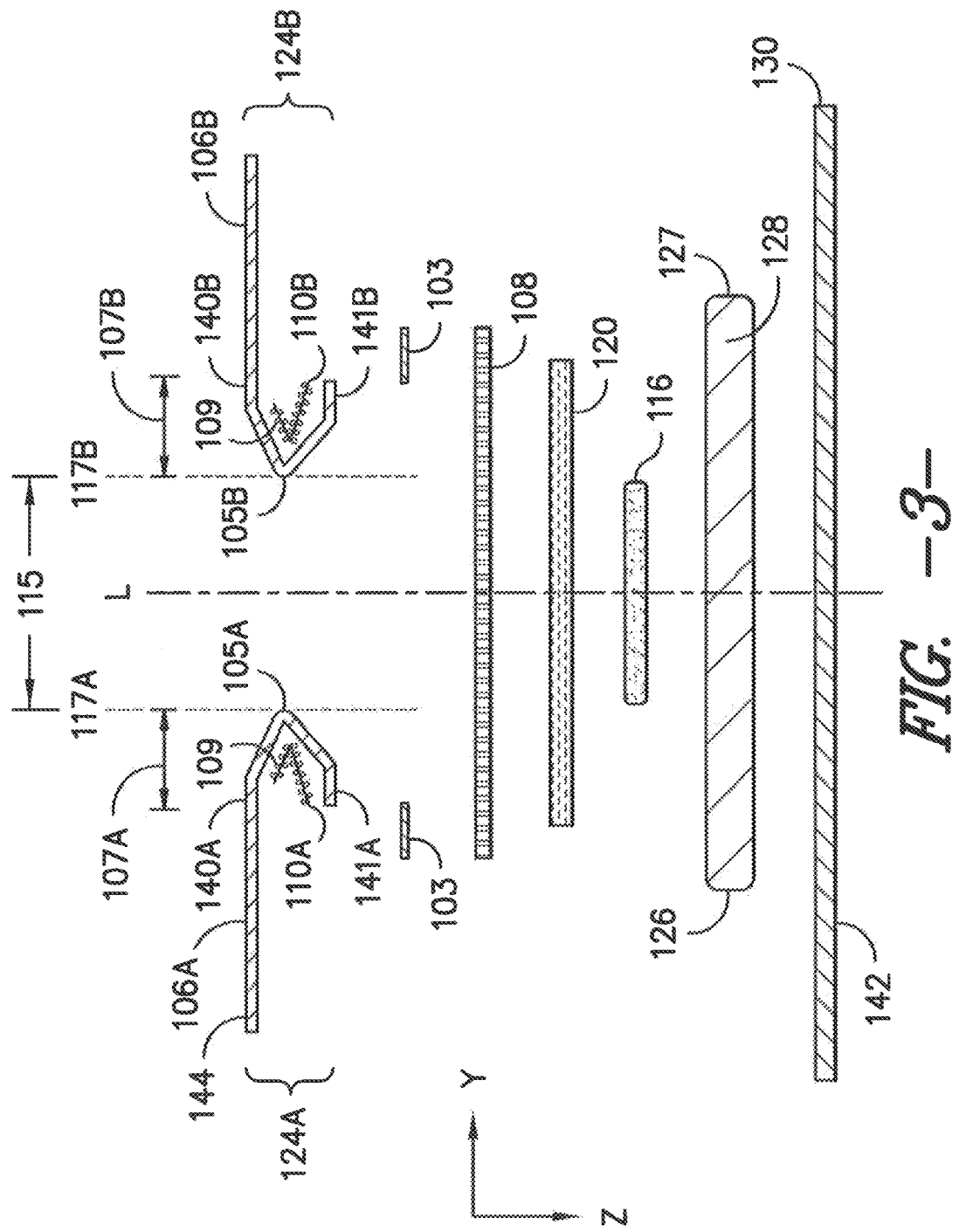
FIG. 3 is an exploded cross-sectional view of one embodiment of the absorbent article of the present disclosure taken at transverse line B of FIG. 1.

After the decolorizing agent carrier material 110A and/or 110B has been treated with the decolorizing agent 109, the decolorizing agent carrier material 110A or 110B can be joined to the side layer 106A or side layer 106B to form laminate 124A or laminate 124B, which ultimately become a part of the topsheet 138 along with the central layer 108. For instance, the decolorizing agent carrier material 110A or 110B can be joined, bonded, adhered, or otherwise laminated the first side layer 106A or the second side layer 106B of the topsheet 138, which can be folded at least once along fold axis 117A or 117B to form fold 105A or 105B, which can define an encapsulated region 107A or 107B that can at least partially envelop the decolorizing agent carrier material 110A or 110B that has been treated with decolorizing agent 109. The folds 105A and 105B can increase bulk in the side layers 106A and 106B, respectively. As shown in FIGS. 3-6 and 9, the decolorizing agent carrier material 110A and decolorizing agent 109 can be at least partially enveloped in an encapsulated region 107A, which can be defined by first fold 105A, where the first fold 105A is formed along longitudinal fold axis 117A to create the encapsulated region 107A. Further, the decolorizing agent carrier material 110B and decolorizing agent 109 can be at least partially enveloped in an encapsulated region 107B, which can be defined by first fold 105B, where the first fold 105B is formed along longitudinal fold axis 117B to create the encapsulated region 107B. As shown in FIG. 3, the first folds 105A and 105B can form encapsulated regions 107A and 107B of the side layers 106A and 106B, in that a second portion 141A of the side layer 106A and a second portion 141B of the side layer 106B can be wrapped around the fold axis 117A or 117B toward the longitudinal centerline L and towards the backsheet 130 in the depth (z) direction at fold 105A or 105B until the second portion 141A and the second portion 141B are generally parallel with a first portion 140A of the side layer 106A and a first portion 140B of the side layer 106B to create an encapsulated or pocket-like structure for containing the decolorizing agent carrier material 110A or 110B and decolorizing agent 109. However, it should be understood that the wrapping can be carried out in any suitable order or by any suitable method so long as an encapsulated region 107A and/or encapsulated region 107B results.

Figure 7:
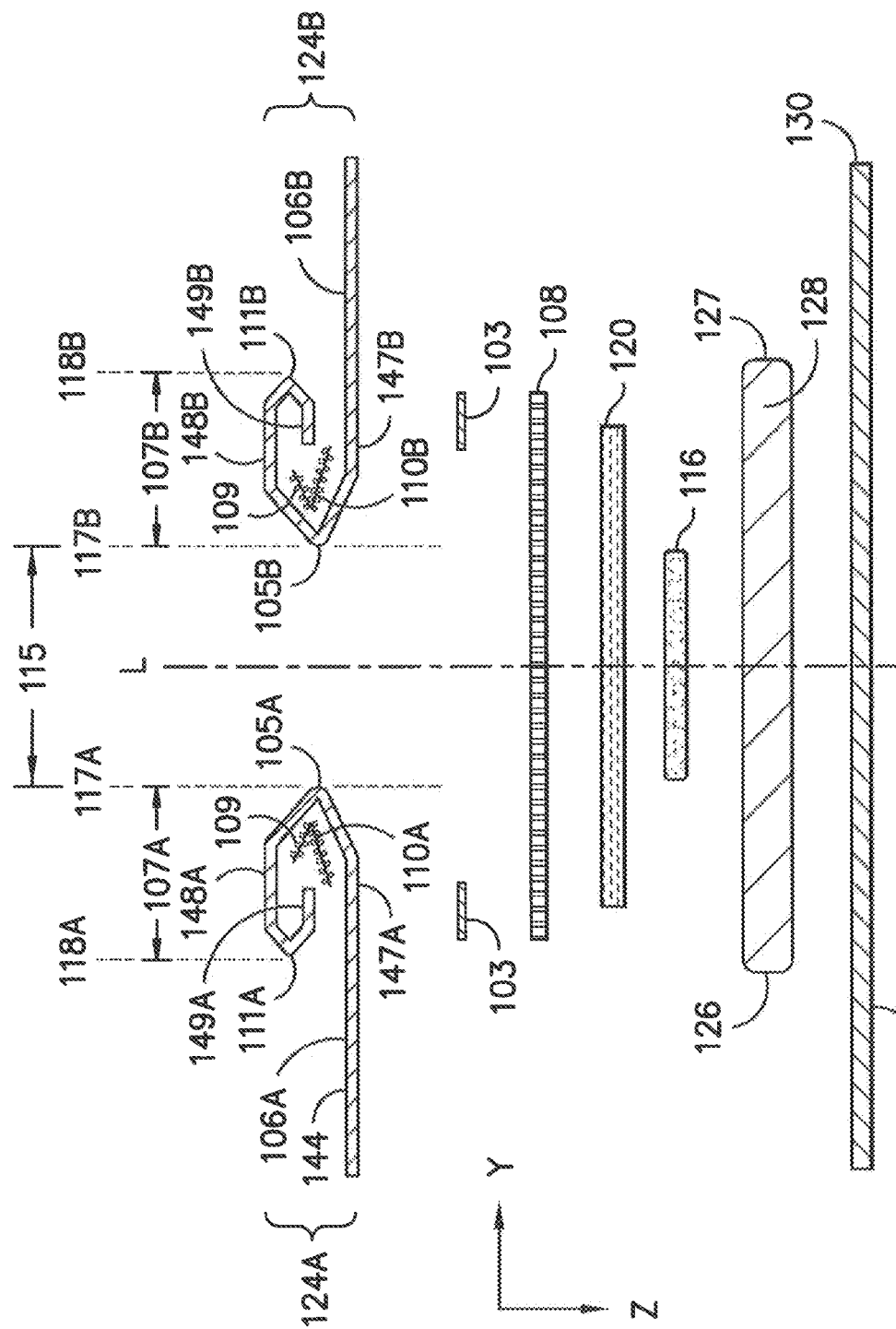
FIG. 7 is an exploded cross-sectional view of yet another embodiment of the absorbent article of the present disclosure taken at transverse line B of FIG. 1.
Figure 8:
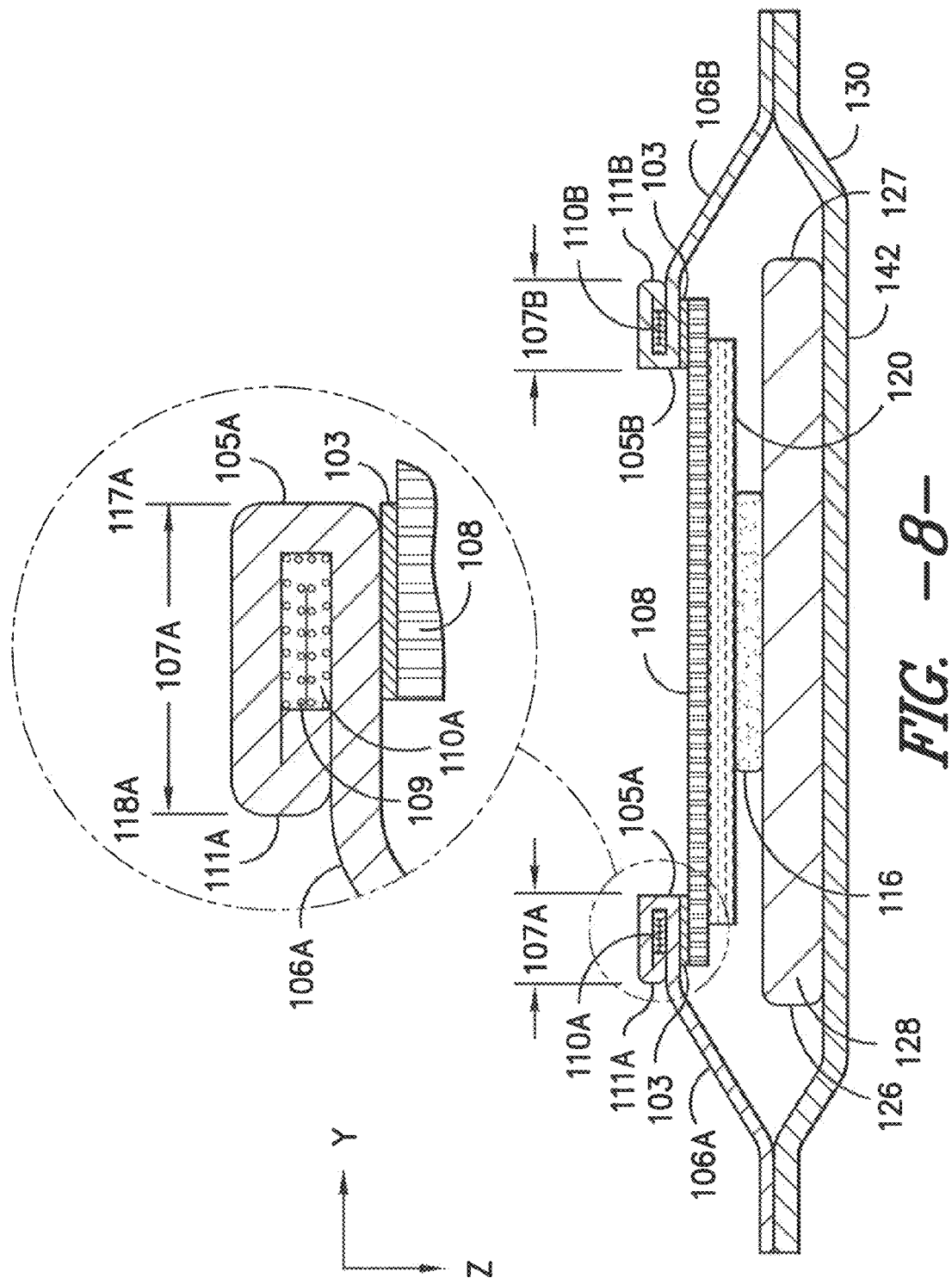
FIG. 8 is a cross-sectional view of the embodiment of the absorbent article shown in FIG. 7 after the absorbent article has been assembled.
Figure 10:
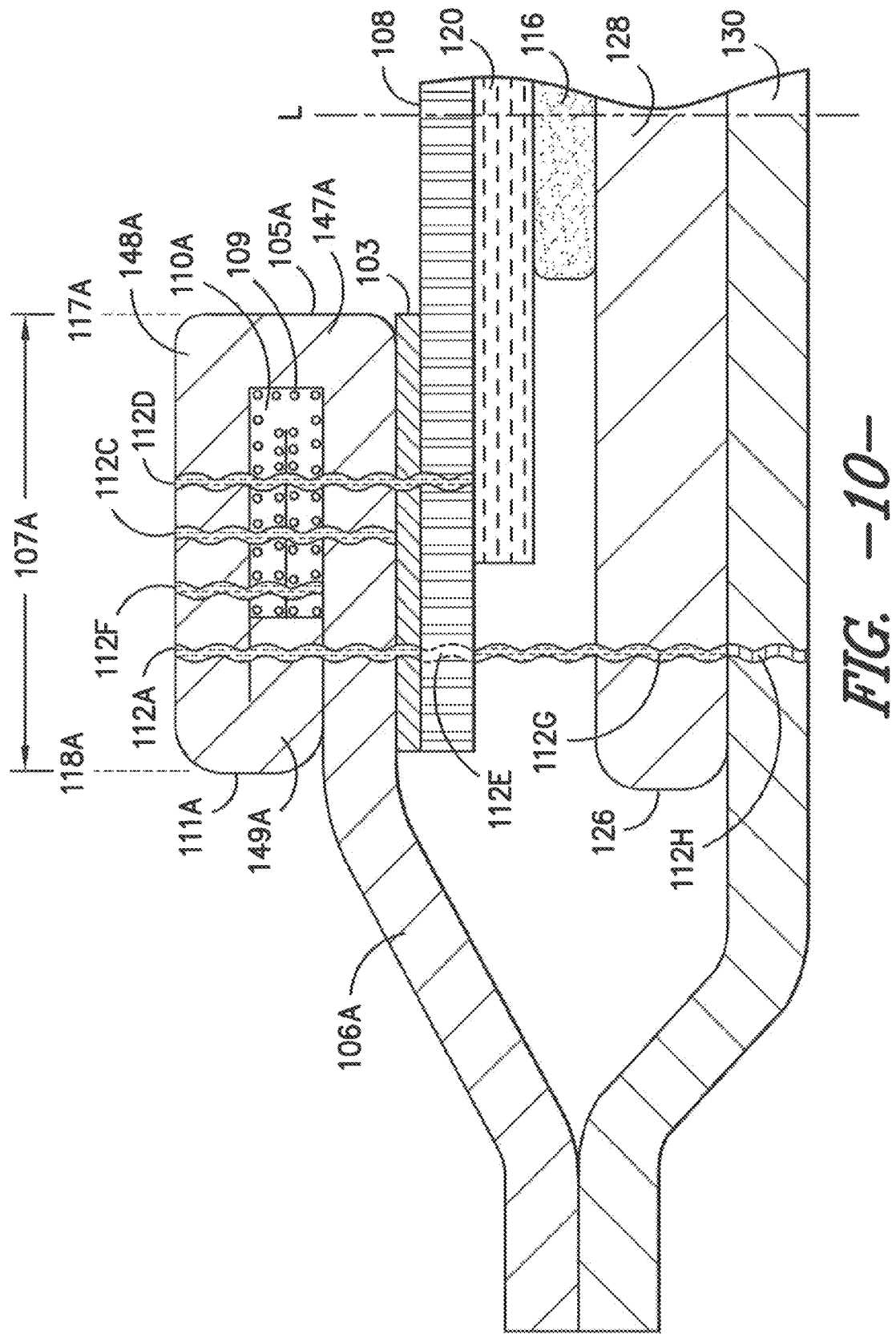
FIG. 10 is a cross-sectional view of one embodiment of the absorbent article of the present disclosure showing various embossing options.

Further, it should be understood that, as shown in FIGS. 7-8 and 10, in other embodiments, the decolorizing agent carrier material 110A and decolorizing agent 109 can be generally fully enveloped in the encapsulated region 107A, such as where a first fold 105A is formed along longitudinal fold axis 117A and a second fold 111A is formed along longitudinal fold axis 118A to create the encapsulated region 107A. Likewise, the decolorizing agent carrier material 110B and decolorizing agent 109 can be generally fully enveloped in the encapsulated region 107B, such as where a first fold 105B is formed along longitudinal fold axis 117B and a second fold 111B is formed along longitudinal fold axis 118B to create the encapsulated region 107B. As shown in FIG. 7, the first folds 105A and 105B and the second folds 111A can form encapsulated regions 107A and 107B of the side layers 106A and 106B. Specifically, a second portion 148A of the side layer 106A and a second portion 148B of the side layer 106B can be wrapped around the fold axis 117A or 117B away from the longitudinal centerline L and away from the backsheet 130 in the depth (z) direction at fold 105A or 105B until the second portion 148A and second portion 148B are generally parallel with a first portion 147A of the side layer 106A and a first portion 147B of the side layer 106B. Then, the second portions 147A and 147B can be wrapped around the fold axis 118A or 118B toward the longitudinal centerline L and towards the backsheet 130 in the depth (z) direction at fold 111A or 111B until a third portion 149A and a third portion 149B are generally parallel with the first portion 147A and the second portion 148A and the first portion 147B and the second portion 148B, respectively. This folding process creates an encapsulated or pocket-like structure for containing the decolorizing agent carrier material 110A or 110B and decolorizing agent 109. However, it should be understood that the wrapping can be carried out in any suitable order or by any suitable method so long as an encapsulated region 107A and/or encapsulated region 107B results.

Regardless of the level or amount of encapsulation of the decolorizing agent carrier material 110A or 110B and decolorizing agent 109 in the encapsulated region 107A or 107B, the decolorizing agent carrier material 110A and/or 110B and decolorizing agent 109 can be contained within an area that is above the absorbent core 128 and that does not extend beyond the periphery or boundary of the absorbent core in the transverse (y) direction. The resulting placement of the decolorizing agent carrier material 110A and 110B in conjunction with decolorizing agent 109 within the encapsulated regions 107A and 107B of the side layers 106A and 106B of the topsheet 138 in reference to other layers of the absorbent article 100 are discussed in more detail below.

Figure 4:
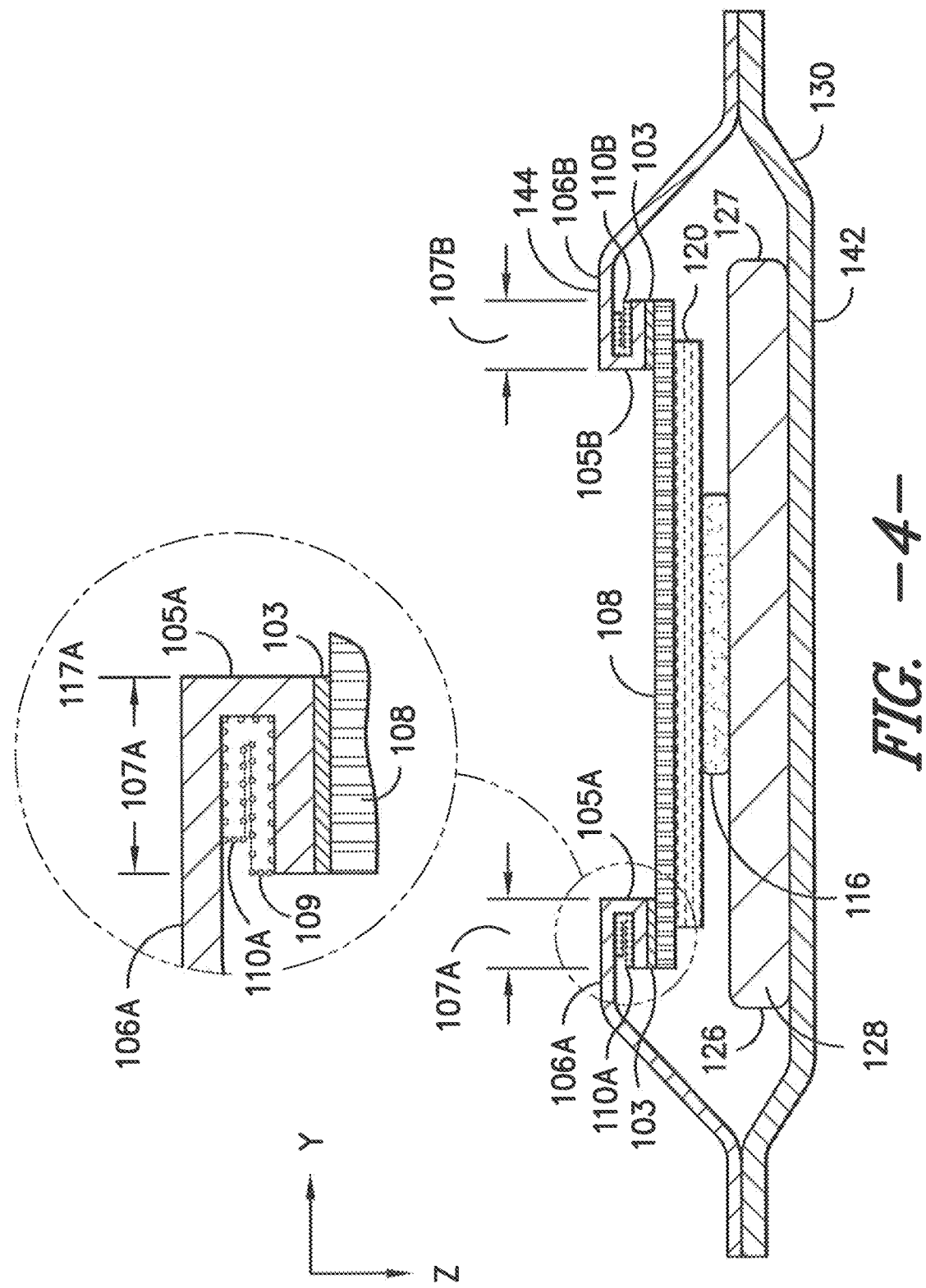
FIG. 4 is a cross-sectional view of the embodiment of the absorbent article shown in FIG. 3 after the absorbent article has been assembled.
Figure 9:
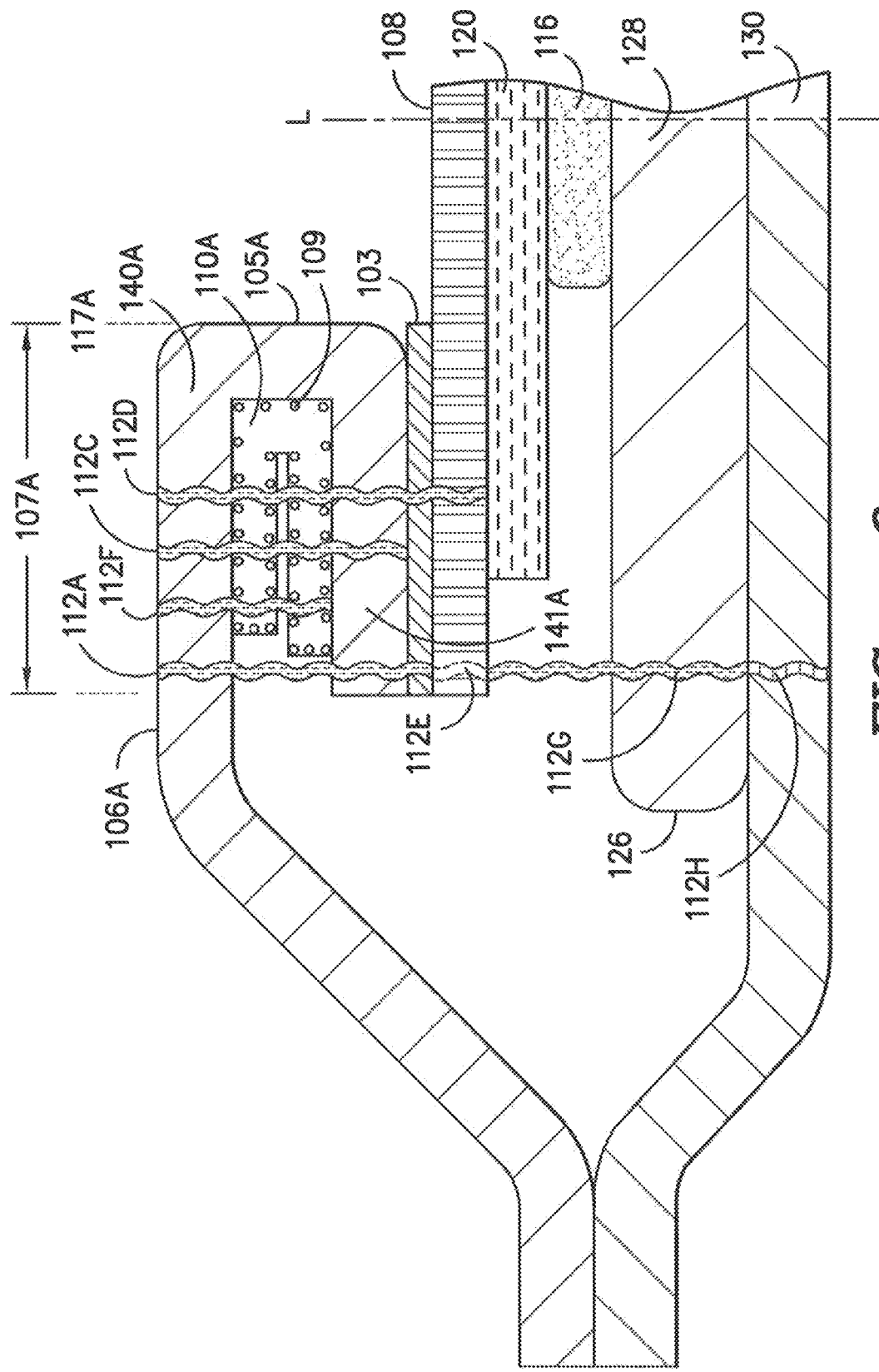
FIG. 9 is a cross-sectional view of one embodiment of the absorbent article of the present disclosure showing various embossing options.

Turning first to FIGS. 3, 4, and 9, an exploded view (FIG. 3), an assembled view (FIG. 4), and an embossed assembled view (FIG. 9) of an absorbent article having an encapsulated region 107A defined by a first fold 105A at a fold axis 117A are shown in more detail. In such an embodiment, after the decolorizing agent carrier material 110A containing the decolorizing agent 109 is adhered to the first side layer 106A, the resulting laminate 124A can be folded as discussed above. Although not shown in the enlarged view of FIG. 9, the same description applies to resulting laminate 124B. For instance, as shown in FIGS. 3 and 9, the first fold 105A creates a first portion 140A of the encapsulated region 107A in first side layer 106A, as well as a second portion 141A, that do not meet such that the encapsulated region 107A partially envelops the decolorizing agent carrier material 110A and decolorizing agent 109 to create bulk in the side layer 106A. The encapsulated region 107A can then be disposed adjacent or above the central layer 108 of the topsheet 138 on one side of the longitudinal centerline L, while the opposing encapsulated region 107B, formed in the same manner and located within the second side layer 106B, is disposed adjacent or above the central layer 108 on the opposing side of the longitudinal centerline L, leaving an exposed portion 115 of the central layer 108 between the opposing side layers 106A and 106B. Thus, in the event that fluid leaks in the lateral direction from the central layer 108 toward the side layers 106A and 106B, the encapsulated region 107A and/or 107B can provide a decolorizing means for altering the color of the fluid to prevent staining via the decolorizing agent 109 contained on or within the decolorizing agent carrier material 110A and/or 110B. After folding and as shown in FIG. 9, embossing can be added to the absorbent article to provide further structural support and prevent stain spreading, as discussed in more detail below. It should be understood, however, that it is not required that the side layers 106A and 106B be folded with the decolorizing agent carrier material 110A and 110B adhered thereto. For instance, the decolorizing agent carrier material 110A and 110B (treated with the decolorizing agent 109) can be applied to the encapsulated regions 107A and 107B via any suitable manner after the side layers 106A and 106B have been folded and may not necessarily align with the folds 105A and 105B of side layers 106A and 106B (not shown).

Figure 5:
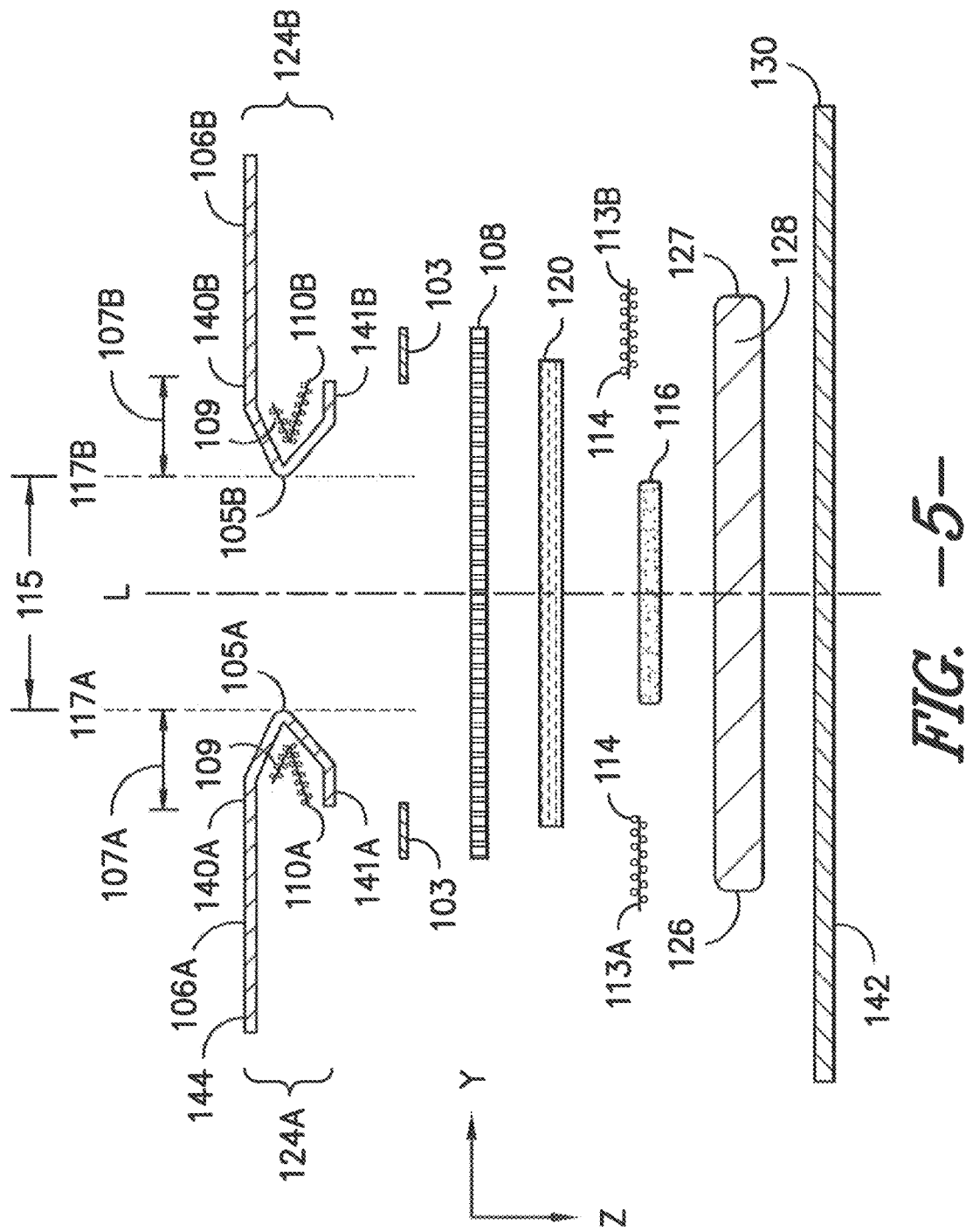
FIG. 5 is an exploded cross-sectional view of another embodiment of the absorbent article of the present disclosure taken at transverse line B of FIG. 1.
Figure 6:
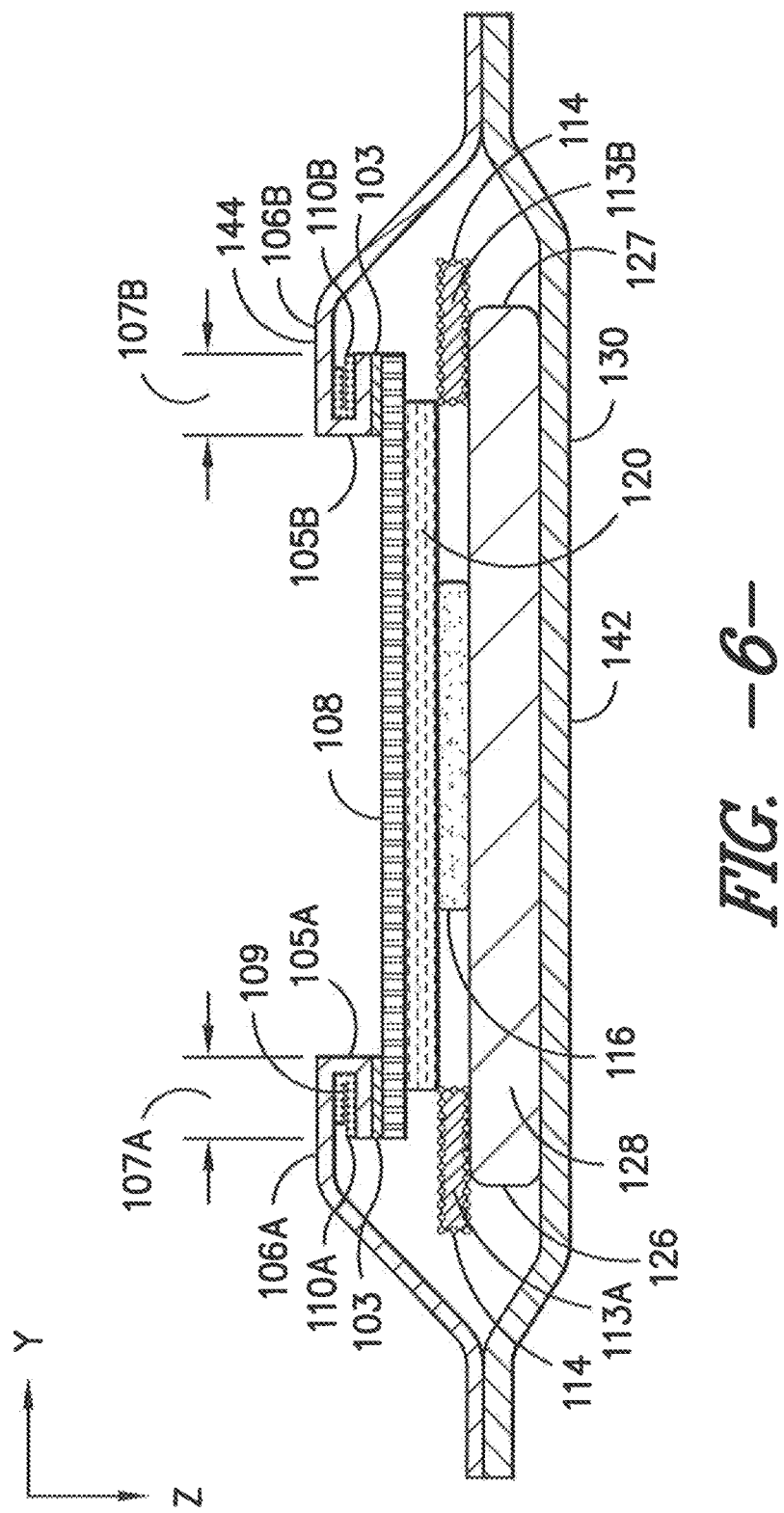
FIG. 6 is a cross-sectional view of the embodiment of the absorbent article shown in FIG. 5 after the absorbent article has been assembled.

Turning next to FIGS. 5 and 6, another embodiment of an absorbent article is shown. The embodiment of FIGS. 5 and 6 has a similar structural arrangement as that shown in FIGS. 3, 4, and 9 as discussed above, except that FIGS. 5 and 6 further show a second decolorizing agent carrier material 113A and 113B and a second decolorizing agent 114 disposed below the side layers 106A and 106B in the depth (z) direction. The second decolorizing agent carrier material 113A and/or 113B as well as the second decolorizing agent 114 can be located adjacent the fluid intake layer 116 and above the periphery of the absorbent core 128 once the absorbent article is assembled. However, it is to be understood that the second decolorizing agent carrier material 113A and/or 113B and the second decolorizing agent 114 can be disposed in any other suitable location within the absorbent article to further prevent staining and leakage of fluid toward the lateral edges of the absorbent article away from the longitudinal centerline L. In addition, in such an arrangement, the second decolorizing agent carrier material 113A and/or 113B can be an MBMF, while the first decolorizing agent carrier material 110A and/or 110B can be a TABCW. Using a TABCW as the decolorizing agent carrier material 110A and/or 110B in the side layers 106A and/or 106B as part of the laminate 124A and/or 124B can create a softer feel than if MBMF is used. Embossing can be carried out in a similar fashion as shown in FIG. 9 as discussed in more detail below. Further, although the embodiments of FIGS. 5 and 6 show a decolorizing agent 109 present on first decolorizing agent carrier materials 110A and 110B, it is to be understood that in some embodiments, such as the embodiment shown in FIGS. 13 and 14, a decolorizing agent 109 is not present on the first decolorizing agent carrier material 110A and/or 110B. Instead, the TABCW carrier material provides bulk in the side layers 106A and 106B and distributes fluid to the second decolorizing agent carrier material 113A and/or 113B (e.g., MBMF layers) below the topsheet 138.

Turning now to FIGS. 7, 8, and 10 an exploded view (FIG. 7), an assembled view (FIG. 8), and an embossed assembled view (FIG. 10) of an absorbent article having a first fold 105A at fold axis 117A and a second fold 111A at fold axis 118A is shown in more detail. In such an embodiment, after the decolorizing agent carrier material 110A containing the decolorizing agent 109 is adhered to first side layer 106A, the resulting laminate 124A can be folded as discussed above. Although not shown in the enlarged view of FIG. 10, the same description applies to resulting laminate 124B. For instance, as shown in FIGS. 7 and 10, the first fold 105A creates a first portion 147A and a second portion 148A, while the second fold 111A further creates a third portion 149A that ultimately meets or contacts the first portion 147A to form a loop-like structure that can completely envelop the decolorizing agent carrier material 110A and decolorizing agent 109 to create bulk in the side layer 106A. The encapsulated region 107A can then be disposed adjacent or above the central layer 108 of the topsheet 138 on one side of the longitudinal centerline L, while the opposing encapsulated region 107B, formed in the same manner and located within the second side layer 106B, is disposed adjacent or above the central layer 108 on the opposing side of the longitudinal centerline L, leaving an exposed portion 115 of the central layer 108 between the opposing side layers 106A and 106B. Thus, in the event that fluid leaks in the lateral direction from the central layer 108 toward the side layers 106A and 106B, the encapsulated region 107A or 107B can provide a decolorizing means for altering the color of the fluid to prevent staining via the decolorizing agent 109 contained on or within the decolorizing agent carrier material 110A and/or 110B. Further, by having two folds, the absorbent article embodied by FIGS. 7, 8, and 10 can have increased bulk compared to the absorbent article embodied by FIGS. 3, 4, 5, 6, and 9 having one fold, which can further enhance the ability of the absorbent article to prevent fluid leakage and staining at the side edges 132 and 134 of the absorbent article. After folding and as shown in FIG. 10, embossing can be added to the absorbent article to provide further structural support and stain prevention capabilities, as discussed in more detail below.

Regardless of the number of folds present in the absorbent article, after the decolorizing agent carrier material 110A and/or 110B containing the decolorizing agent 109 has been joined, bonded, or adhered to the side layers 106A and 106B, the side layers 106A and 106B can be joined to the central layer 108 to form the topsheet 138. It should be understood that the folding of the side layers 106A and/or 106B discussed above can occur before or after joining, bonding, or adhering the side layers 106A and 106B to the central layer 108 to form topsheet 138, depending on the particular configuration. In one particular embodiment, an adhesive 103, such as a construction adhesive, can be used to join the side layers 106A and 106B to the central layer 108 to form the topsheet 138, as shown in FIGS. 2-10. Further, it should be understood that regardless of the number of folds present in the side layers 106A and 106B of the absorbent article, in some embodiments, the decolorizing agent carrier material 110A and/or 110B treated with the decolorizing agent 109 can have a folded width dimension along the transverse (y) direction that is less than or equal to half (50%) of that of a folded width dimension along the transverse (y) direction of the encapsulated regions 107A and 107B of the first side layer 106A and the second side layer 106B, respectively. However, in other embodiments, the decolorizing agent carrier material 110A and/or 110B treated with the decolorizing agent 109 can have a folded width dimension along the transverse (y) direction that greater than half (50%) of that of a folded width dimension along the transverse (y) direction of the encapsulated regions 107A and 107B, such as from about 50% to about 99% of such width. For the purpose of FIG. 1, the decolorizing agent carrier materials 110A and 110B are represented by relatively narrow strips extending in the longitudinal direction to represent that the decolorizing agent carrier materials 110A and 110B have been folded, although this is not required.

In addition to FIGS. 1-10 and 13-14 discussed above, FIGS. 15-20 show other possible embodiments contemplated by the present disclosure where varying fold regions, encapsulated regions, and decolorizing agent carrier material/decolorizing agent configurations are contemplated. For instance, FIG. 15 is a cross-sectional view of one embodiment after the absorbent article has been assembled. Folds 105A and 105B face towards each other and towards the centerline L at the middle of the absorbent article in the transverse (y) direction. The embodiment contemplated by FIG. 15 is similar to the embodiment shown in FIGS. 3 and 4, discussed in detail above, except that the decolorizing agent carrier materials 110A and 110B are not folded, as they are in FIG. 3. FIG. 15 also shows embossed regions 112A and 112B, represented by a curved depression, through various layers of the absorbent article, including the side layers 106A and 106B, the decolorizing agent carrier materials 110A and 110B, and the absorbent core 128. Such embossed regions are discussed in detail below.

Meanwhile, FIG. 16 is an exploded cross-sectional view of one embodiment of the absorbent article of the present disclosure taken at transverse line B of FIG. 1, while FIG. 17 represents the assembled cross-sectional view. First folds 105A and 105B face towards each other and towards the centerline L at the middle of the absorbent article, while second folds 111A and 111B face away from each other and away from the centerline L at the middle of the absorbent article in the transverse (y) direction. The embodiment contemplated by FIGS. 16 and 17 is similar to that shown in FIGS. 7 and 8 except that FIG. 17 also shows embossed regions 112A and 112B, represented by a curved depression, through various layers of the absorbent article, including the side layers 106A and 106B and the absorbent core 128 but not the decolorizing agent carrier materials 110A and 110B. Such embossed regions are discussed in more detail below.

FIG. 18 is an exploded cross-sectional view of another embodiment of the absorbent article of the present disclosure taken at transverse line B of FIG. 1. Like in FIGS. 16 and 17, first folds 105A and 105B face towards each other and towards the centerline L at the middle of the absorbent article, while second folds 111A and 111B face away from each other and away from the centerline L at the middle of the absorbent article in the transverse (y) direction. However, the folding geometry is different as shown in that the decolorizing agent carrier materials 110A and 110B are not folded in FIG. 18. Further, in FIG. 18, the end points 152A and 152B of the encapsulated regions 107A and 107B are in direct contact with the adhesive 103, while in FIG. 16, the endpoints 152A and 152B of encapsulated regions 107A and 107B are separated from the adhesive 103 by a separate portion of the side layers 106A and 106B due to the varying folding geometries.

Further, FIG. 19 is an exploded cross-sectional view of yet another embodiment of the absorbent article of the present disclosure taken at transverse line B of FIG. 1, and FIG. 20 a cross-sectional view of the embodiment of the absorbent article shown in FIG. 19 after the absorbent article has been assembled. The embodiment of FIGS. 19 and 20 contemplates three folds per side of the absorbent article (105A, 111A, and 119A on one side and 105B, 111B, and 119B on the other side as shown). In such an embodiment, the decolorizing agent carrier materials 110A and 110B and decolorizing agent 109 are contained within encapsulated regions 107A and 107B formed by folds 105A and 111A and by 105B and 111B, respectively. Meanwhile, the encapsulated regions 157A and 157B formed by folds 111A and 119A and by 111B and 119B, respectively, do not contain decolorizing agent carrier materials 110A or 110B, or decolorizing agent 109, and function to provide additional bulk to side layers 106A and 106B. In addition and as shown, embossed regions 112A and 112B are formed through the encapsulated regions 157A and 157B, the encapsulated regions 107A and 107B, the decolorizing agent carrier materials 110A and 110B, and the absorbent core 128. Also, it is noted that a portion of the decolorizing agent carrier materials 110A and 110B, and thus the decolorizing agent 109, may come into contact with the absorbent core 128, although a majority of the decolorizing agent carrier materials 110A and 110B, and thus the decolorizing agent 109, are separated from the absorbent core by the encapsulated regions 107A and 107B of the side layers 106A and 106B. In other words, the decolorizing agent carrier materials 110A and 110B, along with the decolorizing agent 109, are only partially separated from the absorbent core 128 in FIGS. 19 and 20, while other embodiments show that the decolorizing agent carrier materials 110A and 110B, along with the decolorizing agent 109 are fully separated from the absorbent core 128.

As can be seen from the various embodiments described above, the decolorizing agent carrier layers 110A and 110B and the decolorizing agent 109 of the various embodiments do not extend laterally beyond and instead can be disposed between or located inside the peripheral edges 126 and 127 of absorbent core layer 128 in the transverse (y) direction when viewed from the body-facing surface 144. In other words, when a cross section of the transverse (y) direction and depth (z) direction is taken of the absorbent article, as shown in FIGS. 3-10 and 13-20, the decolorizing agent carrier material 110A or 110B and/or the decolorizing agent 109 can be positioned above the absorbent core 128 and between the boundaries formed by the peripheral edges 126 and 127 of the absorbent core 128 in the depth (z) direction. However, it is to be understood that in some embodiments (not shown), the decolorizing agent carrier layers 110A and 110B and/or the decolorizing agent 109 may extend beyond the peripheral edges 126 and 127 of the absorbent core 128 toward the side edges 132 and 134 of the absorbent article in the transverse (y) direction when viewed from the body-facing surface 144. It is also to be understood that the encapsulated regions 107A and 107B may also extend beyond the peripheral edges 126 and 127 of the absorbent core 128 in the transverse (y) direction when viewed from the body-facing surface, although the embodiments show the encapsulated regions 107A and 107B as being disposed between the peripheral edges 126 and 127 of the absorbent core 128 in the transverse (y) direction when viewed from the body-facing surface 144 and be positioned above the absorbent core 128 and between the boundaries formed by the peripheral edges 126 and 127 of the absorbent core 128 in the depth (z) direction.

Regardless of whether one fold, two folds, three folds, or more are present to define the boundaries of the encapsulated regions 107A and/or 107B of the side layers 106A and 106B, the encapsulated regions 107A and 107B can have the following dimensions. For instance, when one fold 105A or 105B defines the encapsulated region 107A or 107B of the side layer 106A or 106B, the folded region 107A or 107B can have a width in the transverse (y) direction between medial edge 117A or 117B (which is also first fold axis 117A or 117B in this instance) and lateral edge 118A or 118E (where there is no second fold axis in this instance) that ranges from about 5 mm to about 25 mm, such as from about 7.5 mm to about 20 mm, such as from about 10 mm to about 15 mm. In one particular embodiment, the width can be about 10 mm.

Further, when two folds 105A and 111A (for the first side layer 106A) or 105B and 111B (for the second side layer 106B) are present to define the boundaries of the encapsulated regions 107A and/or 107E of the side layers 106A and 106B, the encapsulated regions 107A and 107B can have a width in the transverse (y) direction between medial edge 117A or 117B (which is also first fold axis 117A or 117B) and lateral edge 118A or 1188 (which is also second fold axis 118A or 1188 in this instance) that ranges from about 5 mm to about 25 mm, such as from about 7.5 mm to about 20 mm, such as from about 10 mm to about 15 mm. In one particular embodiment, the width can be about 15 mm.

Further, the central layer 108 of the topsheet 138 can, in one embodiment, have an overall width in the transverse (y) direction that ranges from about 35 mm to about 75 mm, such as from about 40 mm to about 70 mm, such as from about 50 mm to about 65 mm. In one particular embodiment, the central layer 108 can have an overall width of about 60 mm. Meanwhile, the exposed portion 115 of the central layer 108, that is, the portion of the central layer 108 on which the side layers 106A and 106B are not disposed, can have an overall width in the transverse (y) direction of from about 30 mm to about 60 mm, such as from about 35 mm to about 55 mm, such as from about 40 mm to about 50 mm. In one particular embodiment, the exposed portion of the central layer 108 can have a width in the transverse (y) direction of about 45 mm.

Further, when at least one fold is present on each of the side layers 106A and 106B of the topsheet 138, the shortest distance 151 between the embossed regions 112A and 112B, referring to FIG. 1, which can be present on the opposing side layers 106A and 106B, can range from about 25 mm to about 100 mm, such as from about 40 mm to about 80 mm, such as from about 55 mm to about 75 mm. In one particular embodiment when one fold 105A is present in first side layer 106A and one fold 105B is present in second side layer 106B (as shown in FIGS. 3, 4, 5, 6, and 9), the shortest distance 151 between the embossed regions 112A and 112E in the transverse (y) direction, referring to FIG. 1, can be about 55 mm. Meanwhile, in one particular embodiment when two folds 105A and 111A are present in first side layer 106A and when two folds 105B and 111B are present in second side layer 106B (as shown in FIGS. 7, 8, and 10), the shortest distance 151 between the embossed regions 112A and 112B in the transverse (y) direction, referring to FIG. 1, can be about 60 mm. Meanwhile, the distance between any of the embossed regions 112A-H to the edge 110C or 110F of the decolorizing agent carrier material 110A or 110B can range from about 0 mm to about 10 mm, such as from about 1 mm to about 8 mm, such as from about 2 mm to about 6 mm.

Further, after the absorbent article is assembled as shown in FIGS. 3-8, one or more embossed regions, as represented by 112A, 112B, 112C, 112D, 112E, 112F, 112G, and/or 112H, can be formed in one or more layers of the topsheet 138, as shown in FIGS. 1, 9, and 10, 15, 17, and 20, to create one or more structural barriers. Although the embossed regions 112A and 112B are shown in FIG. 1 as extending the entire length of the absorbent article 100 in the longitudinal (x) direction, this is not required, and it should be understood that the embossed regions may extend only a portion of the length of the absorbent article 100 in the longitudinal (x) direction. Further, although the embossed regions 112A and 112B are represented by a series of discrete points or dots in FIG. 1, this is also not required, and the embossed regions can be in the form of a continuous channel, for example, along the length of the absorbent article in other embodiments. Such embossed regions can form barriers or walls in the depth (z) direction of the absorbent article 100, which can restrict fluid flow towards the edges of the absorbent article, thus reducing the potential for leakage. Such restriction in fluid flow can also increase the dwell time during which fluid, such as menses, is in contact with the decolorizing agent 109, which can enhance the ability of the absorbent article 100 to decolorize the fluid. It is also to be understood that such embossed regions present in the side layers 106A and 106B of the topsheet 138 can extend through to subjacent layers of the absorbent article in the depth (z) direction, such as the portion the central layer 108 that overlaps with the side topsheet layers 106A and 106B, the absorbent core 128, and the backsheet 130, which can add further bulk and fluid control to the absorbent article 100.

Generally, the one or more embossed regions 112A-H can be described as channels formed in the topsheet 138 due to deformation of the topsheet 138. The embossed regions 112A-H can be formed in any suitable pattern to not only create an aesthetically pleasing surface, but also to facilitate intake of bodily fluids in that the fluid will tend to flow along the densified edges of the channels rather than pool on contact points of the topsheet 138. The embossed regions can also assist in funneling bodily fluids toward a desired location in the absorbent article and can prevent leakage towards the periphery of the absorbent article at side edges 132 and 134. The embossed regions may also improve the consistency of the fit properties of the article, both before and after a fluid insult. To provide the absorbent article with such characteristics, the embossed regions 112 may be positioned towards the periphery of the topsheet 138 in either a symmetric or asymmetric manner.

Further, the embossed regions may be formed using any known conventional techniques known in the art. Suitable techniques include, for instance, the use of raised elements to impart the desired embossing pattern to create compressed channels in the topsheet 138. For instance, a suitable process may involve thermal bonding wherein a layer is passed through two rolls (e.g., steel, rubber, etc.) where one is engraved with an embossing pattern and the other is flat. One or both rolls may be heated. In addition, thermal and/or ultrasonic bonding techniques may be employed to create the embossed regions.

As discussed above, at least one embossed region can be present on the topsheet 138 of the absorbent article of the present disclosure. In the embodiments shown in FIGS. 1, 9, and 10, embossed regions 112A, 112B, 112C, 112D, 112E, 112F, 112G, and 112H are shown, Generally, the embossed region(s) 112A-H can function to provide support and structure to the topsheet 138 at the side layers 106A and 106B.

Turning to FIG. 1, embossed regions 112A and 112B run in the longitudinal direction from the distal end 102 to the proximal end 104 of the absorbent article 100 along a lateral edge 118A and a lateral edge 118B, that, if a second fold 111A or 111B is present in the side layers 106A and 106B, also defines the fold axis about which the side layers 106A or 106B are folded to form the encapsulated regions 107A and 107B, as discussed above. Meanwhile, the medial edge 117A and the medial edge 117B remain free of an embossed region and also define the fold axis about which encapsulated regions 107A and 107B are formed, as discussed above. Although the embossed regions 112A and 112B are shown as running the entire length of the absorbent article 100 in the longitudinal (x) direction, it should be understood that in other embodiments, the embossed regions 112A and 112B can run less than the entire length of the absorbent article 100 in the longitudinal (x) direction. Further, while one embossed region 112A is shown on the side layer 106A and one embossed region 112B is shown on the side layer 106B, it is to be understood that more than one embossed region can be present on each side layer 106A and 106B. For instance, 2 embossed regions, 3 embossed regions, 4 embossed regions, 5 embossed regions, etc. can be present on each of the first side layer 106A and the second side layer 106B. Regardless of the number present, the embossed regions of the present disclosure can create one or more structural barriers to prevent the flow of fluids toward the side edges 132 and 134 of the absorbent article 100. Thus, the embossed regions create a "wall" that can hold fluid, such as menses, in the encapsulated regions 107A and 107B of the side layers 106A and 106B for a sufficient amount of time so that the decolorizing agent 109 can decolorize the fluid.

FIGS. 9 and 10 show various embodiments of the absorbent article of the present disclosure and the location of one or more embossed regions 112A, 112C, 112D, 112E, 112F, 112G, and 112H on the encapsulated region 107A of the first side layer 106A of the topsheet 138. Although not shown, it is also to be understood that the same embossed regions 112A, 112C, 112D, 112E, 112F, 112G, and 112H can be present on encapsulated region 107B of side layer 106B. Further, embossed regions 112A, 112C, 112D, 112E, 112F, 112G, and 112H each represent different embossed region configurations that can be utilized, either alone or in combination, and in any order, moving from the lateral edge 118A to the medial edge 117A of the encapsulated region 107A.

Turning now to FIG. 9, which shows a cross section of an absorbent article having a first fold 105A about longitudinal fold axis 117A to define the encapsulated region 107A, embossed regions 112F, 112C, and 112D show that one or more of the embossed regions may be incorporated into the absorbent article at a location that overlaps the decolorizing agent carrier material 110A treated with the decolorizing agent 109. On the other hand, embossed regions 112A and 112E show that one or more of the embossed regions may be incorporated into the absorbent article at a location that is outside the periphery of the decolorizing agent carrier material 11 OA, such as toward the side edges 132 and 134 of the absorbent article, referring to FIGS. 1 and 2, yet still above the peripheral edges 126 and 127 of the absorbent core 128 in the transverse (y) direction when viewed from the body-facing surface 144 of the absorbent article. Each of the embossed regions 112A-H can function to block the spread of fluid from the central layer 108 of the absorbent article toward the edges 132 and 134 of the absorbent article by creating a wall or barrier due to the increased density of the various layers of the absorbent article at the embossed regions 112A-H.

In FIG. 9, embossed regions 112A, 112C, 112D, 112E, 112F, 112G, and 112H also show that the one or more embossed regions can extend through various layers of the absorbent article in the depth (z) direction. For example, embossed region 112A shows that the one or more embossed regions can extend through the encapsulated region 107A of the first side layer 106A from the first (upper) portion 140A through to the second (lower) portion 140E of the side layer 106A, where, as discussed above, such portions are formed due to folding of the first side layer 106A about the first longitudinal fold axis 117A. On the other hand, embossed region 112E shows that in some embodiments, embossed region 112A can be extended further through the adhesive 103 and the central layer 108 of the topsheet layer 138. Further, embossed region 112G shows that any of the embossed regions present can be extended through the absorbent core 128, and embossed region 112H shows that any of the embossed regions present can be extended to the backsheet 130. Meanwhile, embossed region 112F shows that in some embodiments, one or more embossed regions can extend through the first (upper) portion 140A of the first side layer 106A and through the decolorizing agent carrier material 110A, but not through to the second (lower) portion 141A of the first side layer 106A, while embossed region 112C shows that in some embodiments, one or more embossed regions can extend through the first (upper) portion 140A of the side layer 106A, through the decolorizing agent carrier material 110A, and through the second (lower) portion 141A of the side layer 106A. Then, embossed region 112D shows that in some embodiments, one or more embossed regions can extend through the first (upper) portion 140A of the side layer 106A, through the decolorizing agent carrier material 110A, through the second (lower) portion 141A of the side layer 106A, through the adhesive 103, and through the central layer 108. Regardless of the number of embossed regions or the kind of layers through which such regions extend in the depth (z) direction, it is to be understood that at least a portion of the decolorizing agent carrier material 110A and decolorizing agent 109 remains free of embossing toward the longitudinal centerline L so that it is not blocked from contacting any fluid, such as menses, that may leak from the topsheet or other regions of the absorbent article so that the decolorizing agent can decolorize the fluid.

Turning next to FIG. 10, which shows a cross section of an absorbent article having a first fold 105A about longitudinal fold axis 117A and a second fold 111A about longitudinal fold axis 118A to define the encapsulated region 107A, embossed regions 112F, 112C, and 112D show that one or more of the embossed regions may be incorporated into the absorbent article at a location that overlaps the decolorizing agent carrier material 110A treated with the decolorizing agent 109. On the other hand, embossed regions 112A and 112E show that one or more of the embossed regions may be incorporated into the absorbent article at a location that is outside the periphery of the decolorizing agent carrier material 110A, such as toward the side edges 132 and 134 of the absorbent article, referring to FIG. 1, yet still above the periphery or boundary of the absorbent core 128.

In FIG. 10, embossed regions 112A, 112C, 112D, 112E, 112F, 112G, and 112H also show that the one or more embossed regions can extend various through various layers of the absorbent article in the depth (z) direction. For example, embossed region 112A shows that the one or more embossed regions can extend through the encapsulated region 107A of the first side layer 106A from the second (upper) portion 148A through to the third (middle) portion 149A of the side layer 106A and then through to the first (lower) portion 147A, where, as discussed above, such portions are formed due to folding of the first side layer 106A about the first longitudinal fold axis 117A and the second longitudinal fold axis 118A. On the other hand, embossed region 112E shows that in some embodiments, embossed region 112A can be extended further through the adhesive 103 and the central layer 108 of the topsheet layer 138. Further, embossed region 112G shows that any of the embossed regions present can be extended through the absorbent core 128, and embossed region 112H shows that any of the embossed regions present can be extended to the backsheet 130. Meanwhile, embossed region 112F shows that in some embodiments, one or more embossed regions can extend through the second (upper) portion 148A of the first side layer 106A and through the decolorizing agent carrier material 110A, but not through to the first (lower) portion 147A of the first side layer 106A, while embossed region 112C shows that in some embodiments, one or more embossed regions can extend through the second (upper) portion 148A of the side layer 106A, through the decolorizing agent carrier material 110A, and through the first (lower) portion 147A of the side layer 106A. Then, embossed region 112D shows that in some embodiments, one or more embossed regions can extend through the second (upper) portion 148A of the side layer 106A, through the decolorizing agent carrier material 110A, through the first (lower) portion 147A of the side layer 106A, through the adhesive 103, and through the central layer 108. Again, regardless of the number of embossed regions or the kind of layers through which such regions extend in the depth (z) direction, it is to be understood that at least a portion of the decolorizing agent carrier material 110A and decolorizing agent 109 remains free of embossing toward the longitudinal centerline L so that it is not blocked from contacting any fluid, such as menses, that may leak from the topsheet or other regions of the absorbent article so that the decolorizing agent can decolorize the fluid.

Transfer Delay Layer

As shown in FIGS. 2-10, the absorbent article can also include a liquid-permeable transfer delay layer 120 positioned below the topsheet layer 138 in the depth (z) direction. The transfer delay layer 120 may contain a material that is substantially hydrophobic. For example, the transfer delay layer may be a nonwoven fibrous web composed of a relatively hydrophobic material, such as polypropylene, polyethylene, polyester or the like, and also may be composed of a blend of such materials. One example of a material suitable for the transfer delay layer is a spunbond web composed of polypropylene, multi-lobal fibers. Further examples of suitable transfer delay layer materials include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay layer are described in U.S. Pat. No. 4,798,603 to Meyer, et al. and U.S. Pat. No. 5,248,309 to Serbiak, et al. To adjust the performance of the invention, the transfer delay layer 120 may also be treated with a selected amount of surfactant to increase its initial wettability. The transfer delay layer 120 may generally have any size, such as a length of about 150 mm to about 300 mm. Typically, the length of the transfer delay layer 120 is approximately equal to the length of the absorbent article 100. The width of the transfer delay layer 120 may be from between about 50 mm to about 75 mm, and particularly about 48 mm. The transfer delay layer 120 typically has a basis weight less than that of the other absorbent members. For example, the basis weight of the transfer delay layer 120 is typically less than about 250 grams per square meter (gsm), and in some embodiments, between about 40 gsm to about 200 gsm.

Airlaid Layer

As shown in the various embodiments, the absorbent article can also contain a liquid-permeable intake layer positioned between the central layer of the topsheet and the absorbent core layer. For instance, in FIGS. 1 and 2, the feminine hygienic pad 100 can include an additional fluid intake layer 116 that is disposed between the topsheet 138 and the absorbent core 128. Such an intake layer may be made of a material that is capable of rapidly transferring, in the D-direction, body fluid that is delivered to the central layer 108. The intake layer may generally have any shape and/or size desired. In one embodiment, the intake layer can have a curved rectangular shape, with a length equal to or less than the overall length of the feminine hygienic pad 100, and a width less than the width of the feminine hygienic pad 100. For example, a length of between about 150 mm to about 300 mm and a width of between about 10 mm to about 60 mm may be utilized. Any of a variety of different materials are capable of being used for the intake layer to accomplish the above-mentioned functions. The material may be synthetic, cellulosic, or a combination of synthetic and cellulosic materials. For example, airlaid cellulosic tissues may be suitable for use in the intake layer. The airlaid cellulosic tissue may have a basis weight ranging from about 10 gsm to about 300 gsm, and in some embodiments, between about 100 gsm to about 250 gsm. In one embodiment, the airlaid cellulosic tissue has a basis weight of about 200 gsm. The airlaid tissue may be formed from hardwood and/or softwood fibers. An airlaid tissue has a fine pore structure and provides an excellent wicking capacity, especially for menses.

Additionally, to further enhance the ability of the absorbent article to transfer bodily fluid in the depth (z) direction from its body-facing surface 144 toward any lower layers in the absorbent article as well as to enhance the ability of the fluid intake layer 116 to conform to the wearer's body based on its ability to bend, the fluid intake layer 116 can have an opening 150. The opening 150 can be of any suitable shape, such as ovular, circular, rectangular, square, triangular, etc. The opening 150 in the first fluid intake layer 116 can serve to funnel and direct bodily fluid away from the body-facing surface 144 of the absorbent article and towards lower layers of the absorbent article in the depth (z) direction. The opening 150 can also form a cup or well-like structure for holding fluid and preventing its leakage away from a central region of the absorbent article and towards the edges.

Absorbent Core

As discussed above in relation to the position of the decolorizing agent carrier material and decolorizing agent, an absorbent core 128 can be disposed between the topsheet 138 and the backsheet 130 (discussed below). However, it is also to be understood that in some embodiments (not shown), there may not be a separate absorbent core layer 128. The absorbent core 128 can generally be any single layer structure or combination of layer components, which desirably demonstrate some level of compressibility, conformability, are non-irritating to a wearer's skin, and capable of absorbing and retaining liquids and certain other body wastes. Additionally, the absorbent core 128 can provide additional capacity to absorb and retain bodily exudates such as menses. The absorbent core 128 may be formed from a variety of different materials and contain any number of desired layers. For example, the absorbent core 128 typically includes one or more layers (e.g., two layers) of an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a particular embodiment, the absorbent web material includes a matrix of cellulosic fluff, and may also include superabsorbent material. The cellulosic fluff may comprise a blend of wood pulp fluff. One preferred type of fluff is identified with the trade designation NB 416, available from Weyerhaeuser Corp., and is a bleached, highly absorbent wood pulp containing primarily soft wood fibers.

If desired, the absorbent core 128 can include an optional amount of superabsorbent materials. Examples of suitable superabsorbent materials include poly(acrylic acid) and poly (methacrylic acid), poly(acrylamides), poly(vinyl ethers), maleic anhydride copolymers with vinyl ethers and α-olefins, poly(vinyl pyrrolidone), poly(vinylmorpholinone), poly(vinyl alcohol), and salts and copolymers thereof. Other superabsorbent materials include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum, and so forth. Mixtures of natural and wholly or partially synthetic superabsorbent polymers may also be useful in the present invention. The superabsorbent material can be present in the absorbent core 128 in any amount as desired.

Regardless of the combination of absorbent materials used in the absorbent core 128, the absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. A coform nonwoven material may also be employed. Methods and apparatus for carrying out such techniques are well known in the art.

Backsheet

Furthermore, in the illustrated embodiments, in addition to the layers discussed above, the absorbent article also includes a liquid impermeable backsheet 130. The backsheet 130 is generally liquid impermeable and defines a garment-facing surface 142 of the absorbent article. The backsheet 130 may permit the passage of air or vapor out of the absorbent article, while still blocking the passage of liquids. Any liquid impermeable material may generally be utilized to form the backsheet 130. For example, one suitable material that may be utilized is a microporous polymeric film, such as a polyolefin film of polyethylene or polypropylene. In particular embodiments, a polyethylene film is utilized that has a thickness in the range of about 0.2 mils to about 5.0 mils, and particularly between about 0.5 to about 3.0 mils. A specific example of a backsheet material is a polyethylene film such as that obtainable from Pliant Corporation, Schaumburg, Ill., USA. Another example would include calcium carbonate-filled polypropylene film. In still a further embodiment, the backsheet may be a hydrophobic nonwoven material with water barrier properties such as a nonwoven laminate, an example of which would be a spunbond, meltblown, meltblown, spunbond, four-layered, laminate. The backsheet 130 may therefore be of a single or multiple layer construction, such as of multiple film layers or laminates of film and nonwoven fibrous layers. Even with a film backsheet, a nonwoven fibrous layer may be used as the undergarment facing surface for better "hand" or feel.

Additional Layers

Additional layers between the topsheet layer and the absorbent core layer include surge layers as are commonly known. Surge layers (not shown) can be constructed of any woven or nonwoven material that is easily penetrated by bodily exudates. The surge layers can help to absorb, decelerate, and diffuse surges or gushes of liquid that may be rapidly introduced into the absorbent article 100. The surge layers can rapidly accept and temporarily hold the liquid prior to releasing the liquid into, for instance, the absorbent core 128 or any other layer of the absorbent article. Various woven fabrics and nonwoven webs can be used to construct the surge layers. For example, the surge layers may comprise a nonwoven fabric layer composed of a meltblown or spunbond web of polyolefin or polyester filaments. Such nonwoven fabric layers may include conjugate, biconstituent and homopolymer fibers of staple or other lengths and mixtures of such fibers with other types of fibers. The surge layers can also be a bonded carded web or an airlaid web composed of natural and/or synthetic fibers. The bonded carded web may, for example, be a powder bonded carded web, an infrared bonded carded web, or a through-air bonded carded web. The bonded carded webs can optionally include a mixture or blend of different fibers. The surge layers typically have a basis weight of less than about 100 gsm, and in some embodiments, from about 10 gsm to about 40 gsm.

Still another layer that may be present between the topsheet layer and the absorbent core layer includes a bicomponent fluid distribution layer BFDL (not shown), which increases absorbency by providing a high void space and may be made of a TABCW, having a basis weight in one embodiment of between about 25 and 100 gsm. Further, while side wings 136A and 136B are shown as formed from extensions of the backsheet 130 and the side layers 106A and 106B such that they are integral portions of the absorbent article 100, they may also be later-attached, non-integral structures. As an additional, but optional feature to the embodiments described, lines of polymeric material may be applied along the edges of, or adjacent the edges, of any of the described layers (not shown). Such polymeric material may be applied to either the body-facing surface or the garment-facing surface of the layers, so as to create an additional hydrophobic barrier to stop or retard the flow of a spreading menses stain.

In summary, it has been found that feminine pad leakage often results from residual absorbent article menses insults on or near the multi-layered topsheet, body-facing surface of an absorbent article. Such residual insult either is not contained by the absorbent layer(s) as a result of fluid saturation of the layer or impeded flow of an insult into the absorbent core. By "impeded", it is meant that such flow is either slowed or restricted as a result of the design or arrangement of the absorbent article, or, alternatively, not absorbed quickly enough as a result of a sudden insult. Such impeded flow can result in run-off of insult from the absorbent article, even when the absorbent layer is not saturated. With the development of, and popularity of progressively thinner and smaller (surface area) feminine care pads and liners, the potential for leakage has been amplified. Depending on design features, such pads may have less overall capacity, having smaller absorbent areas. When an absorbent layer is saturated, the menses insult can pool on the surface of the pad which can subsequently run off the side edges of the pad to a garment or bedding, or be transferred via body contact to a garment or bedding. As runoff and pooling are often the immediate causes of staining in thinner feminine pads, the present disclosure has addressed such causes by directing fluid flow not only in absorbent layers, but also in non-absorbent layers at side edges of an absorbent article. Further, the present disclosure has assisted in reducing overall topsheet layer stain size as a result of both decolorizing agents on the side layers of the topsheet and the use of structural barriers, such as at least one fold and embossing, in conjunction with such decolorizing agents. Such reduction in stain size has led to smaller topsheet layer stain sizes, and relatively larger, interiorly-situated or absorbent core layer stain sizes (overall stain size surface area) when compared to the topsheet layer stain size. Such reduced color (in lateral pad areas) and reduced stain size, can help provide comfort, and instill confidence to some consumers who wear such absorbent products. Finally, by separating color producing components of menses within the feminine hygienic pad, by use of a strategically placed and constructed decolorizing agent-containing layer (or layers), lower viscosity components of menses may be absorbed more efficiently by the absorbent core layer structures.

By employing the structural barriers discussed above, such as at least one encapsulated region and embossing, which can provide a wall to block or slow the spread of menses flow to the side edges of the absorbent article, in combination with the decolorizing agents described herein, color can be discharged from potentially stain-producing exudates at the edges of the product, and desirably off of the topsheet layer, where leakage is most likely to occur in modern feminine-hygiene absorbent articles. As such, interior regions of the product may be left substantially untreated with the decolorizing agents, thereby, allowing the decolorizing agents to target menses at specific peripheral structures. Such a configuration enables a user to observe and inspect the bodily exudates in the center of the product, and also allows the decolorizing agents to be applied only to those portions of the product needed to achieve the desired effect so that the untreated regions/portions can continue to fulfill their functions, such as absorbing or wicking fluids, etc. without undue stiffness or sacrifice in comfort. In addition, the use of targeted decolorizing agents at certain regions/portions of the article provides additional emotional comfort to users who prefer not to view the spread of menses insult stains, and while also seeking comfort in knowing that leakage that may result from such absorbent article will result in less visibly apparent staining on a garment or bedding.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalent thereto.

What is claimed is:

1. A feminine care absorbent article extending in a longitudinal direction, a transverse direction, and a depth direction, wherein the longitudinal direction defines a distal end and a proximal end, and wherein the feminine care absorbent article comprises:
   a liquid permeable topsheet, wherein the liquid permeable topsheet comprises a longitudinally extending central layer positioned adjacent a first longitudinally extending side layer and a second longitudinally extending side layer in the transverse direction, wherein the first side layer includes a first encapsulated region, wherein the first encapsutlated region is defined by a first located about a first fold axis, the first fold axis extending in the longitudinal direction, wherein the encapsulated region at least partially envelops a first decolorizing agent carrier material treated with a first decolorizing agent for decolorizing menses, and further wherein at least one layer of the topsheet defines a body-facing surface of the feminine care absorbent article; and
   a liquid impermeable backsheet, wherein the liquid impermeable backsheet defines a garment-facing surface.

2. The feminine care absorbent article of claim 1, further comprising an absorbent core having first and second peripheral edges disposed between the topsheet and the backsheet in the transverse direction.

3. The feminine care absorbent article of claim 2, wherein the first encapsulated region is disposed between the first and second peripheral edges of the absorbent core in the transverse direction when viewed from the body-facing surface.

4. The feminine care absorbent article of claim 1, wherein the first side layer includes at least one embossed region extending in the longitudinal direction and extending in the depth direction through at least a part of the first encapsulated region.

5. The feminine care absorbent article of claim 4, wherein the embossed region is present continuously from the distal end to the proximal end of the feminine care absorbent article in the longitudinal direction.

6. The feminine care absorbent article of claim 1, wherein the first decolorizing agent carrier material treated with the first decolorizing agent is free of embossing.

7. The feminine care absorbent article of claim 1, wherein the first decolorizing agent carrier material treated with the first decolorizing agent has a width dimension along the transverse direction that is less than or equal to half of that of a width dimension along the transverse direction of the first encapsulated region.

8. The feminine care absorbent article of claim 1, wherein the first encapsulated region is further defined by a second fold located about a second fold axis, the second fold axis extending in the longitudinal direction.

9. The feminine care absorbent article of claim 8, wherein the at least one embossed region is present in only one of the first fold and the second fold.

10. The feminine care absorbent article of claim 1, wherein the first encapsulated region envelops substantially all of the first decolorizing agent carrier material treated with the first decolorizing agent.

11. The feminine care absorbent article of claim 1, wherein the first decolorizing agent comprises polyethylene glycol, polyethylene oxide, methoxypolyethylene glycol, ammonium sulfate, zinc oxide, carbomer, or a combination thereof.

12. The feminine care absorbent article of claim 1, wherein the first decolorizing agent carrier material comprises a meltblown microfiber.

13. The feminine care absorbent article of claim 1, wherein the first decolorizing agent carrier material comprises a through-air bonded carded web.

14. The feminine care absorbent article of claim 1, wherein the second side layer includes a second encapsulated region, wherein the second encapsulated region at least partially envelops a second decolorizing agent carrier material treated with a second decolorizing agent for decolorizing menses.

15. The feminine care absorbent article of claim 14, wherein the second side layer includes at least one embossed region extending in the longitudinal direction and extending in the depth direction through at least a part of the second encapsulated region.

16. The feminine care absorbent article of claim 1, wherein the feminine care absorbent article further comprises an additional decolorizing agent carrier material treated with an additional decolorizing agent, wherein the additional deodorizing agent carder material is positioned between the topsheet and backsheet in the depth direction.

17. The feminine care absorbent article of claim 1, wherein the first side layer and the second side layer include a hydrophobic coating.

* * * * *